United States Patent
Honma et al.

(10) Patent No.: US 6,645,743 B1
(45) Date of Patent: Nov. 11, 2003

(54) POLYHYDROXYALKANOATE COPOLYMER CONTAINING IN MOLECULE UNIT WITH VINYLPHENYL STRUCTURE IN ITS SIDE CHAIN AND METHOD OF MANUFACTURING THE SAME

(75) Inventors: Tsutomu Honma, Kanagawa (JP); Etsuko Sugawa, Kanagawa (JP); Tetsuya Yano, Kanagawa (JP); Takeshi Imamura, Kanagawa (JP); Takashi Kenmoku, Kanagawa (JP); Tatsuki Fukui, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/372,285

(22) Filed: Feb. 25, 2003

(30) Foreign Application Priority Data

| Feb. 28, 2002 | (JP) | 2002-054897 |
| Dec. 13, 2002 | (JP) | 2002-362962 |
| Feb. 14, 2003 | (JP) | 2003-037322 |

(51) Int. Cl.⁷ ............... C12P 7/42; C08G 63/06; C08F 20/00
(52) U.S. Cl. ............ 435/146; 528/361; 528/363; 528/364; 528/365; 528/373; 528/378; 528/380; 528/422; 525/450; 525/535; 525/540; 524/732; 524/734; 524/770; 524/773; 435/135; 435/253.3; 435/255.1; 435/874; 435/877
(58) Field of Search ................ 528/361, 363, 528/364, 365, 373, 378, 380, 422; 525/450, 535, 540; 524/732, 734, 770, 773; 435/135, 146, 253.3, 255.1, 874, 877

(56) References Cited

U.S. PATENT DOCUMENTS

| 2001/0029039 A1 | 10/2001 | Honma et al. ............ 435/135 |
| 2002/0052444 A1 | 5/2002 | Imamura et al. ........... 525/107 |
| 2002/0160467 A1 | 10/2002 | Honma et al. ............ 435/135 |

FOREIGN PATENT DOCUMENTS

| EP | 1 188 782 A2 | 3/2002 |
| EP | 1 236 752 A2 | 9/2002 |
| JP | 59-190945 | 10/1984 |
| JP | 2000-72865 | 3/2000 |
| JP | 2001-288256 | 10/2001 |

OTHER PUBLICATIONS

Katharina Fritzsche et al., "An Unusual Bacterial Polyester with a Phenyl Pendant Group," 191 *Makromol. Chem.* 1957–1965 (1990).

Y.B. Kim et al., "Preparation and Characterization of Poly(β–hydroxyalkanoates) Obtained from *Pseudomonas oleovorans* Grown with Mixtures of 5–Phenylvaleric Acid and n–Alkanoic Acids," 24 *Macromol.* 5256–5260 (1991).

Joanne M. Curley et al., "Production of Poly(3–hydroxyalkanoates) Containing Aromatic Substituents by *Pseudomonas oleovorans*," 29 *Macromol.* 1762–1766 (1996).

(List continued on next page.)

*Primary Examiner*—Samuel A. Acquah
(74) *Attorney, Agent, or Firm*—Fitzpatrick, Cella, Harper & Scinto

(57) ABSTRACT

A polyhydroxyalkanoate (PHA) having a desired configuration is produced using a raw material containing ω-(4-vinylphenyl)-alkanoic acid and ω-substituted alkanoic acid in which a group having a ring structure selected from phenyl, thienyl, and cyclohexyl structures substitutes therefor on the end thereof by producing a PHA copolymer containing the corresponding 3-hydroxy-ω-(4-vinylphenyl)-alkanoate unit and the corresponding 3-hydroxy-ω-substituted alkanoate unit by making use of a microorganism capable of producing the PHA or by oxidizing a predetermined portion of the corresponding PHA.

16 Claims, 7 Drawing Sheets

OTHER PUBLICATIONS

Suzette M. Aróstegui et al., "Bacteria Polyesters Produced by *Psuedomonas oleovorans* Containing Nitrophenyl Groups," 32 *Macromol.* 2889–2895 (1999).

Helmut Ritter et al., "Bacterial Production of Polyesters Bearing Phenoxy Groups in the Side Chain, 1 Poly(3–hydroxy–5–phenoxypentanoate–co–3–hydroxy–9–phenoxy–nonanoate) from *Pseudomonas oleovorans*," 195 *Macromol. Chem. Phys.* 1665–1672 (1994).

Ohyoung Kim et al., "Bioengineering of Poly(β–hydroxyalkanoates) for Advanced Material Applications: Incorporation of Cyano and Nitrophenoxy Side Chain Substituents," 41 (Supp. 1) *Can. J. Microbiol.* 32–43 (1995).

Richard A. Gross et al., "Cyanophenoxy–Containing Microbal Polyesters: Structural Analysis, Thermal Properties, Second Harmonic Generation and In–Vivo Biodegradability," 39 *Polymer International* 205–213 (1996).

M.Y. Lee et al., "Hydrophilic Bacterial Polyesters Modified with Pendant Hydroxyl Groups," 41 *Polymer* 1703–1709 (2000).

Won Ho Park et al., "Epoxidation of Bacterial Polyesters with Unsaturated Side Chains. I. Production and Epoxidation of Polyesters From 10–Undecanoic Acid," 31 *Macromol.* 1480–1486 (1998).

Moon Yeun Lee et al., "Crosslinking of Microbal Copolyesters with Pendant Epoxide Groups by Diamine," 40 *Polymer* 3787–3793 (1999).

G.J.M. de Koning et al., "A Biodegradable Rubber by Crosslinking Poly(Hydroxyalkanoate) From *Pseudomonas oleovorans*," 35(10) *Polymer* 2090–2097 (1994).

J.K. Stille et al., "Tetracyclic Dienes. I. The Diels–Alder Adduct of Norbornadiene and Cyclopentadiene," 81 *J. Am. Chem. Soc.* 4273–4275 (Aug. 1959).

Herbert Ulmer et al., "Bacterial Production of Poly(β–hydroxyalkanoates) Containing Unsaturated Repeating Units by *Rhodospirillum rubrum*," 27 *Macromol.* 1675–1679 (1994).

Marianela Andújar et al., "Polyesters Produced by *Pseudomonal oleovorans* Containing Cyclohexyl Groups," 30 *Macromol.* 1611–1615 (1997).

Alexander Steinbüchel et al., "Diversity of Bacterial Polyhydroxyalcanoic Acids," 128 *FEMS Microbiol. Lett.* 219–228 (1995).

European Search Report in Application No. 03004350.9 (May 6, 2003).

POLYHYDROXYALKANOATE COPOLYMER CONTAINING IN MOLECULE UNIT WITH VINYLPHENYL STRUCTURE IN ITS SIDE CHAIN AND METHOD OF MANUFACTURING THE SAME

BACKGROUND OF THE INVENTION

1. Field of the Invention

The present invention relates to a polyhydroxyalkanoate copolymer that contains a novel unit, and a method of manufacturing the same utilizing microorganisms.

2. Related Background Art

Heretofore, it has been reported that many microorganisms produce poly-3-hydroxybutyrate (PHB) or other polyhydroxyalkanoate (PHA) and accumulate the products in their microbial bodies ("Biodegradable Plastics Handbook", Biodegradable Plastics Society, Ed., pp. 178–197, (1995) published by NTS Co., Ltd., JAPAN). Polymers such as PHA produced by microorganisms can be used for manufacturing various kinds of products by melting process and so on just as in the case of the conventional plastics. Furthermore, polymers such as PHA produced by microorganisms are biodegradable, so that there is an advantage in that they can be completely decomposed by microorganisms in nature. Therefore, PHA or the like originated from microorganisms has no tendency to remain as it is in the natural environment when it is disposed. It means that it will not become a factor of causing environmental pollution while many of the conventional synthetic polymer compounds become factors thereof. Furthermore, the microorganism-produced PHA has an excellent biocompatibility in general, so that it has been expected that it would be used in many applications such as a medical soft structural member.

It has been also known that the microorganism-produced PHA would have various compositions and configurations depending on the species of microorganisms used in the production, the formulations of culture media, culture conditions, and so on. Up to now, from the viewpoint of mainly improving the physical properties of PHA, studies on control of the composition and configuration of the microorganism-produced PHA have been carried out.

As one of the studies which have been made aiming at controlling the composition or configuration of the microorganism-produced PHA, in recent years, the attempts to produce PHA having an aromatic ring in its unit from a microorganism have been extensively conducted.

In each of "Makromol. Chem.", 191, 1957–1965 (1990) and "Macromolecules", 24, 5256–5260 (1991), it is reported that Pseudomonas oleovorans uses 5-phenyl-valeric acid as a substrate to produce PHA that contains 3-hydroxy-5-phenyl-valerate as a unit thereof. In "Macromolecules", 29, 1762–1766 (1996), it is reported that Pseudomonas oleovorans uses 5-(p-tolyl)-valeric acid as a substrate and produces PHA that contains 3-hydroxy-5-(p-tolyl)-valerate as a unit thereof. In "Macromolecules", 32, 2889–2895 (1999), furthermore, it is reported that Pseudomonas oleovorans uses 5-(2,4-dinitrophenyl)-valeric acid as a substrate to produce PHA that contains two different units: 3-hyroxy-5-(2,4-dinitrophenyl)-valerate and 3-hydroxy-5-(p-nitrophenyl)-valerate. Furthermore, in "Macromol. Chem. Phys.", 195, 1665–1672 (1994), it is reported that Pseudomonas oleovorans uses 11-phenoxy-undecanoic acid as a substrate to produce a PHA copolymer that contains two different units: 3-hydroxy-5-phenoxy-valerate and 3-hydroxy-9-phenoxy-nonanoate.

Furthermore, JP 2989175 B discloses the invention relating to: a homopolymer that contains a unit of 3-hydroxy-5-(monofluorophenoxy)-pentanoate (3H5(MFP)P) or a unit of 3-hydroxy-5-(difluorophenoxy)-pentanoate (3H5(DFP)P); a copolymer that contains at least the 3H5(MFP)P unit or the 3H5(DFP)P unit; Pseudomonas putida having the abilities of producing these polymers; and a method of manufacturing the above polymers using genus Pseudomonas. In addition, Japanese Patent Publication No. 2989175 describes as an effect of the invention that a polymer that contains a unit obtained by the substitution of phenoxy groups having one or two substituted fluorine atoms on the end of a side chain can be synthesized by utilizing long-chain fatty acids having substituents. In addition, it is also described that such a polymer keeps a good processability in addition to its high melting point, and further described that such a polymer can be provided with stereoregularity and water repellency.

In addition to the study of PHA that contains in its structural unit a fluorine-substituted aromatic ring group with a fluorine substituent on its aromatic ring, the study of PHA that contains in its structural unit a substituted aromatic ring group having a substituted cyano or nitro group on its aromatic ring is reported.

Furthermore, "Can. J. Microbiol.", 41, 32–43 (1995) and "Polymer International", 39, 205–213 (1996) report the production of PHA that contains a monomer unit of 3-hydroxy-6-(p-cyanophenoxy)-hexanoate or 3-hydroxy-6-(p-nitrophenoxy)-hexanoate from Pseudomonas oleovorans ATCC29347 strain and Pseudomonas putida KT2442 strain using octanoic acid and 6-(p-cyanophenoxy)-hexanoic acid or 6-(p-nitrophenoxy)-hexanoic acid as substrates, respectively.

These PHAs, which contain units having aromatic rings with substituents thereon, keep their own polymer properties derived from the aromatic rings, such as high glass-transition temperatures and good processabilities. In addition, these PHAs are provided with additional functions derived from the substituents on the aromatic rings. Therefore, the PHAs become multi-functional PHAs.

On the other hand, for preparing multi-functional PHA by introducing any functional group into the side chain of the produced polymer by a chemical conversion using the vinyl group, studies have been also extensively conducted on the basis of PHA that contains a structural unit having a vinyl group on its side chain.

In "Polymer", 41, 1703–1709 (2000), it is reported that polyester having a hydroxyl group on its side chain is produced by producing polyester having a vinyl group on its side chain using Pseudomonas oleovorans and oxidizing the vinyl group in the molecule of the polyester.

Similarly, in "Macromolecules", 31, 1480–1486 (1998), reported is the production of polyester having an epoxy group on its side chain by producing polyester having a vinyl group on its side chain using Pseudomonas oleovorans and epoxidizing the vinyl group.

In "Polymer", 40, 3787–3793 (1999), furthermore, polymer having an epoxy group on its side chain, which is obtained by the same method as described above, is subjected to a crosslinking reaction by heating it together with hexamethylene diamine. In this document, such a reaction and the results of analyzing the reaction product are reported.

Furthermore, in "Polymer", 35, 2090–2097 (1994), reported is the study of improving the physical properties of polyester, in which a vinyl group on the side chain of the polyester is used to permit a crosslinking reaction in the molecule of polyester.

SUMMARY OF THE INVENTION

As is evident from these conventional studies listed above, as the vinyl group is an unsaturated hydrocarbon group, the vinyl group shows a high reactivity in an addition reaction or the like and is capable of introducing various kinds of functional groups and conducting chemical conversion. Furthermore, the vinyl group on the side chain of the polymer would be a stepping stone to the crosslinking reaction of the polymer, i.e., a crosslinking point. Therefore, the vinyl group provided in the structural unit of PHA can be very useful for considering the range of applications of polymer as a functional material.

In each of these conventionally reported polyhydroxyalkanoates that contain structural units having vinyl groups on their side chains, the structural unit has a structure in which a vinyl group is substituted at the end of an alkyl side chain directly bonded to a polyhydroxyalkanoate main chain skeleton, for example, a 3-hydroxy-ω-vinyl-alkanoate unit. However, as with an alkyl chain on which a vinyl group is substituted at the end thereof, the thermal characteristics of polyhydroxyalkanoate having a side chain with a straight carbon chain skeleton are not always preferable (e.g., glass transition temperature and melting point are not generally so high) for melting process. For providing films, processed products, and so on, the number of existing materials having excellent desired characteristics is not always satisfactory. Furthermore, most of conventionally reported polyhydroxyalkanoates or the like containing a structural unit having a vinyl group on its side chain is generated as a copolymer also containing a 3-hydroxy-alkanoate unit having a straight alkyl side chain as an additional unit. Therefore, the content ratio of the additional 3-hydroxy-alkanoate unit is one of the factors that lower the processability.

By contrast, as described above, a high glass transition temperature can be generally observed in polyhydroxyalkanoate that contains a structural unit having an aromatic ring on its side chain because of the presence of the aromatic ring. Thus, the polyhydroxyalkanoate has good properties as a processed product.

In other words, for developing a novel functional polymer having an excellent processability, it is desirable to utilize polyhydroxyalkanoate that contains a structural unit having both of a vinyl group and an aromatic ring on its side chain. Considering the enlargement of the field of applications and uses, it is also desirable to utilize a polyhydroxyalkanoate copolymer that contains an additional structural unit that is capable of controlling the physical properties (e.g., thermal properties) of polyhydroxyalkanoate in addition to a structural unit that contains both of an aromatic ring and a vinyl group on its side chain. However, heretofore, there is no report of a polyhydroxyalkanoate copolymer that contains in the same molecule an additional structural unit that is capable of regulating the physical properties (e.g., thermal properties) of polyhydroxyalkanoate in addition to a structural unit that contains both of an aromatic ring and a vinyl group on its side chain.

An object of the present invention is to provide a novel polyhydroxyalkanoate copolymer including: a structural unit having an aromatic ring and a vinyl group on its side chain; and another kind of structural unit capable of controlling physical properties (e.g., thermal properties) of the copolymer as an additional structural unit in the same molecule, and also provide a method of manufacturing such a novel copolymer.

As a result of intensive studies for solving the above problems, the present inventors have found that a copolymer having a high glass transition temperature and good properties as a processed product due to a benzene ring of 4-vinylphenyl group is obtained when a 3-hydroxy-ω-(4-vinylphenyl)-alkanoate unit is employed as a structural unit contained in a polyhydroxyalkanoate copolymer, and in addition the copolymer becomes one capable of controlling its physical properties such as thermal properties when it contains a 3-hydroxy-ω-substituted alkanoate unit obtained by substituting a group containing a ring structure selected from the group consisting of a phenyl structure, a thienyl structure, and a cyclohexyl structure for the end of its side chain. The present inventors have found that the vinyl group existing as a 4-vinylphenyl group can be used as a highly reactive atomic group at the time of an introduction of various kinds of functional groups, a chemical conversion, and a crosslinking reaction of polymer. Furthermore, the present inventors have also confirmed that it is possible to allow a microorganism having the ability of PHA production to produce a copolymer including a 3-hydroxy-ω-(4-vinylphenyl)-alkanoate unit and a 3-hydroxy-ω-substituted alkanoate unit in the same molecule, which can be obtained by using (4-vinylphenyl)-alkanoic acid as a substrate to be converted to the corresponding 3-hydroxy-ω-(4-vinylphenyl)-alkanoate acid unit and simultaneously using ω-substituted alkanoic acid, in which a group containing a ring structure selected from the group consisting of a phenyl structure, a thienyl structure, and a cyclohexyl structure is substituted at the end thereof, as a substrate to be converted to the corresponding 3-hydroxy-ω-substituted alkanoate unit. Based on these series of findings, the present invention has been ultimately completed.

That is, the present invention relates to a polyhydroxyalkanoate copolymer including in the same molecule:

a 3-hydroxy-ω-(4-vinylphenyl)-alkanoate unit represented by the general formula (1):

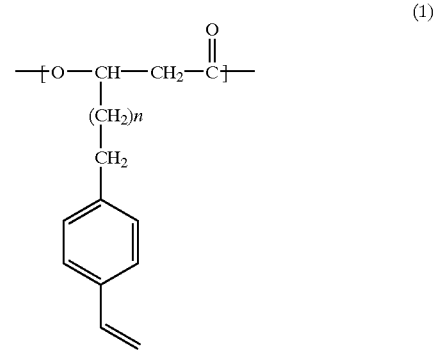

where n represents an integer of 0 to 7, and n independently represents the integer for each unit when the plural units are present; and at least one unit selected from the group consisting of: a 3-hydroxy-ω-substituted alkanoate unit represented by the general formula (2):

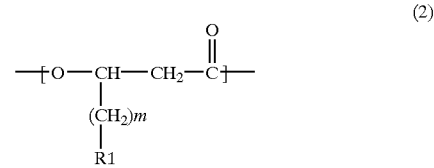

where m represents an integer of 1 to 8 and $R_1$ represents a group having a residue with a ring structure selected from a phenyl structure and a thienyl structure; and a 3-hydroxy-ω-cyclohexyl-alkanoate unit represented by the general formula (3):

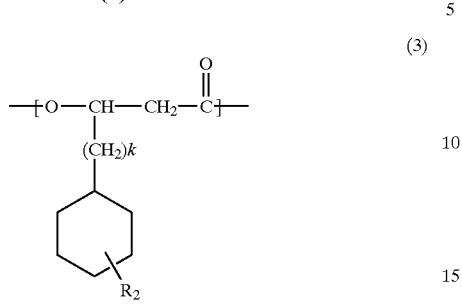

(3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which m and $R_1$ independently represent the integer and the group, respectively, for each unit when the plural units represented by the general formula (2) are present, and k and $R_2$ independently represent the integer and the substituent, respectively, for each unit when the plural units represented by the general formula (3) are present.

According to one aspect of the present invention, the invention relates to a method of manufacturing a polyhydroxyalkanoate copolymer that contains in the same molecule:

a 3-hydroxy-ω-(4-vinylphenyl)-alkanoate unit represented by the general formula (1):

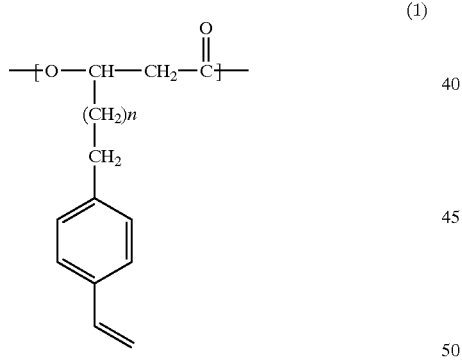

(1)

where n represents an integer of 0 to 7, and n independently represents the integer for each unit when the plural units are present; and at least one unit selected from the group consisting of: a 3-hydroxy-ω-substituted alkanoate unit represented by the general formula (19):

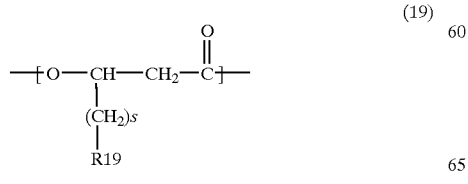

(19)

where s represents an integer of 1 to 8 and $R_{19}$ represents a group having a residue with a ring structure selected from a phenyl structure and a thienyl structure; and a 3-hydroxy-ω-cyclohexyl-alkanoate unit represented by the general formula (3):

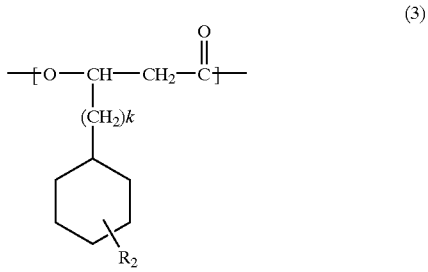

(3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which s and $R_{19}$ independently represent the integer and the group, respectively, for each unit when the plural units represented by the general formula (19) are used, and k and $R_2$ independently represent the integer and the substituent, respectively, for each unit when the plural units represented by the general formula (3) are present, the method including:

allowing a microorganism capable of synthesizing the polyhydroxyalkanoate copolymer from a raw material to synthesize the polyhydroxyalkanoate by making the microorganism act on the raw material including:

(A) at least one ω-(4-vinylphenyl)-alkanoic acid represented by the following general formula (16):

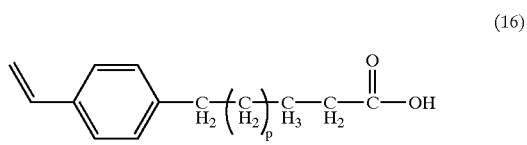

(16)

where p represents an integer of 0 to 7; and (B) at least one component selected from the group consisting of ω-substituted alkanoic acid represented by the general formula (17):

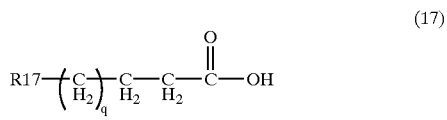

(17)

where q represents an integer of 1 to 8, and $R_{17}$ represents a group containing a residue with a ring structure selected from a phenyl structure and a thienyl structure, and ω-cyclohexyl-alkanoic acid represented by the general formula (18):

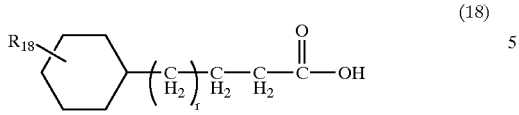
(18)

where $R_{18}$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and r represents an integer of 0 to 8.

According to another aspect of the present invention, the invention relates to a method of manufacturing a polyhydroxyalkanoate that contains in the same molecule:

at least a 3-hydroxy-ω-(4-vinylphenyl)-alkanoate unit represented by the general formula (1):

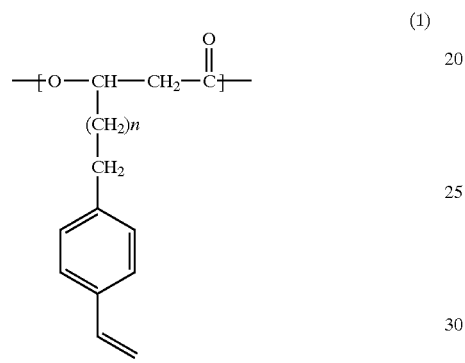
(1)

where n represents an integer of 0 to 7, and n independently represents the integer for each unit when the plural units represented by the general formula (1) are present; and at least one unit selected from the group consisting of a 3-hydroxy-ω-substituted alkanoate unit represented by the general formula (2):

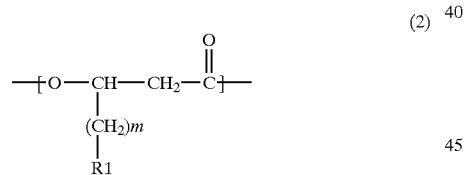
(2)

where m represents an integer of 1 to 8, and $R_1$ represents a group containing a residue with a ring structure selected from a phenyl structure and a thienyl structure, and a 3-hydroxy-ω-cyclohexyl-alkanoate unit represented by the general formula (3):

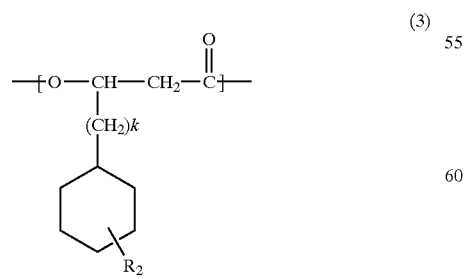
(3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which m and $R_1$ independently represent the integer and the group, respectively, for each unit when the plural units represented by the general formula (2) are present, and k and $R_2$ independently represent the integer and the substituent, respectively, for each unit when the plural units represented by the general formula (3) are present, the $R_1$ containing at least a group selected from the group consisting of a substituted phenyl group represented by the following general formula (4'), an unsubstituted or substituted phenylsulfinyl group represented by the general formula (12), and an unsubstituted or substituted phenylsulfonyl group represented by the general formula (13):

(4')

where $R_3'$ represents $COOR_4$ ($R_4$ represents a hydrogen atom, a sodium atom, or a potassium atom);

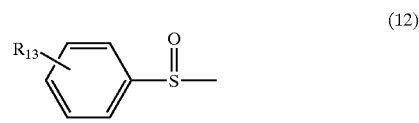
(12)

where $R_{13}$ represents a hydrogen atom, a halogen atom, a CN group, an $NO_2$ group, $COOR_{14}$, $SO_2R_{15}$ ($R_{14}$ represents H, Na, K, $CH_3$, or $C_2H_5$, and $R_{15}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group; and

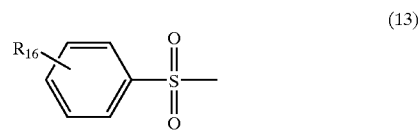
(13)

where $R_{16}$ represents a hydrogen atom, a halogen atom, a CN group, an $NO_2$ group, $COOR_{17}$, $SO_2R_{18}$ ($R_{17}$ represents H, Na, K, $CH_3$, or $C_2H_5$, and $R_{18}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group, the method including one of the steps of:
(a) oxidizing a part of a vinyl group contained in a phenyl group of a group represented by the general formula (1) of a raw material to form the group represented by the general formula (4') as the $R_1$, with the raw material including a polyhydroxyalkanoate copolymer containing in the same molecule:

two or more 3-hydroxy-ω-(4-vinylphenyl)-alkanoate units represented by the general formula (1):

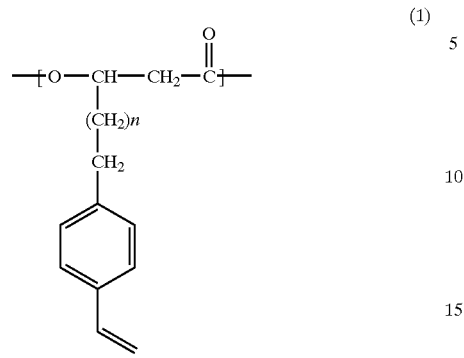

(1)

where n represents an integer of 0 to 7, and n independently represents the integer for each unit; and at least one unit selected from the group consisting of a 3-hydroxy-ω-substituted alkanoate unit represented by the general formula (19):

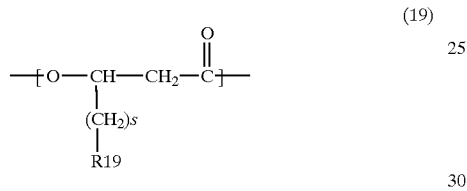

(19)

where s represents an integer of 1 to 8 and $R_{19}$ represents a group having a residue with a ring structure selected from a phenyl structure and a thienyl structure, and a 3-hydroxy-ω-cyclohexyl-alkanoate unit represented by the general formula (3):

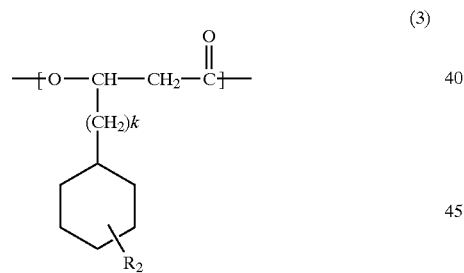

(3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which s and $R_{19}$ independently represent the integer and the group, respectively, for each unit when the plural units represented by the general formula (19) are present, and k and $R_2$ independently represent the integer and the substituent, respectively, for each unit when the plural units represented by the general formula (3) are present; and (b) selectively oxidizing —S— of the substituent represented by the general formula (7) in a polyhydroxyalkanoate copolymer provided as a raw material to be converted to a group represented by the general formula (12) or a group represented by the general formula (13), with the polyhydroxyalkanoate copolymer containing in the same molecule: a 3-hydroxy-ω-(4-vinylphenyl)-alkanoate unit represented by the general formula (1):

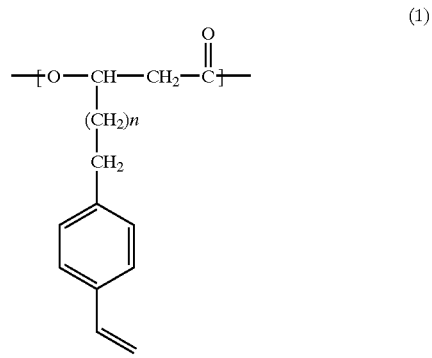

(1)

where n represents an integer of 0 to 7, and n independently represents the integer for each unit when the plural units represented by the general formula (1) are present; and at least one unit selected from the group consisting of a 3-hydroxy-ω-substituted alkanoate unit represented by the general formula (2):

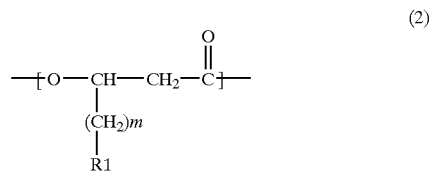

(2)

where m represents an integer of 1 to 8, and $R_1$ represents an unsubstituted or substituted phenylsulfanyl group represented by the general formula (7):

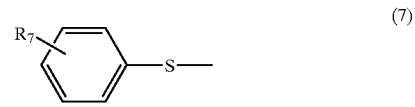

(7)

where $R_7$ represents a hydrogen atom, a halogen atom, a CN group, an $NO_2$ group, $COOR_8$, $SO_2R_9$ ($R_8$ represents H, Na, K, $CH_3$, or $C_2H_5$, and $R_9$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group, and a 3-hydroxy-ω-cyclohexyl-alkanoate unit represented by the general formula (3):

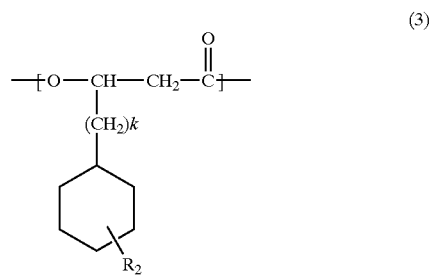

(3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which m and $R_1$ independently represent the integer and the group, respectively, for each unit when the plural units represented by the general formula (2) are present, and k and $R_2$ independently represent the integer and the substituent, respectively, for each unit when the plural units represented by the general formula (3) are present.

That is, the polyhydroxyalkanoate copolymer in accordance with the present invention includes: a unit component (i) composed of at least a 3-hydroxy-ω-(4-vinylphenyl)-alkanoate unit represented by the above general formula (1); and a unit component (ii) composed of at least one selected from the group consisting of a 3-hydroxy-ω-substituted alkanoate unit represented by the above general formula (2) and a 3-hydroxy-ω-cyclohexyl-alkanoate unit represented by the above general formula (3) in the same molecule. That is, the polyhydroxyalkanoate copolymer in accordance with the present invention includes at least a 3-hydroxy-ω-(4-vinylphenyl)-alkanoate unit represented by the above general formula (1) as a unit component (i) and at least unit selected from the group consisting of a 3-hydroxy-ω-substituted alkanoate unit represented by the above general formula (2) and a 3-hydroxy-ω-cyclohexyl-alkanoate unit represented by the above general formula (3) as a unit component (ii) in the same molecule. Here, if the unit component (i) contains two or more units, these units may include same or different units. If the unit component (ii) contains two or more units, furthermore, these units may include same or different units.

In the polyhydroxyalkanoate copolymer according to the present invention, it is preferable that the $R_1$ in the general formula (2) is a group selected from the group consisting of:

an unsubstituted or substituted phenyl group represented by the general formula (4):

(4)

where $R_3$ represents a hydrogen atom, a halogen atom, a CN group, an $NO_2$ group, a $CH_3$ group, a $C_2H_5$ group, a $C_3H_7$ group, $COOR_4$ ($R_4$ represents a hydrogen atom, a sodium atom, or a potassium atom), a $CF_3$ group, a $C_2F_5$ group, or a $C_3F_7$ group;

an unsubstituted or substituted phenoxy group represented by the general formula (5):

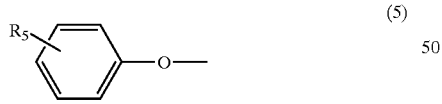

(5)

where $R_5$ represents a hydrogen atom, a halogen atom, a CN group, an $NO_2$ group, a $CH_3$ group, a $C_2H_5$ group, a $C_3H_7$ group, an $SCH_3$ group, a $CF_3$ group, a $C_2F_5$ group, or a $C_3F_7$ group;

an unsubstituted or substituted benzoyl group represented by the general formula (6):

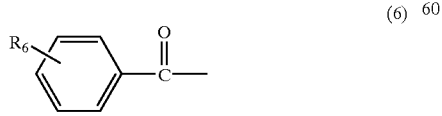

(6)

where $R_6$ represents a hydrogen atom, a halogen atom, a CN group, an $NO_2$ group, a $CH_3$ group, a $C_2H_5$ group, a $C_3H_7$ group, a $CF_3$ group, a $C_2F_5$ group, or a $C_3F_7$ group;

an unsubstituted or substituted phenylsulfanyl group represented by the general formula (7):

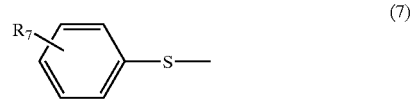

(7)

where $R_7$ represents a hydrogen atom, a halogen atom, a CN group, an $NO_2$ group, $COOR_8$, $SO_2R_9$ ($R_8$ represents H, Na, K, $CH_3$, or $C_2H_5$, and $R_9$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group;

an unsubstituted or substituted (phenylmethyl)-sulfanyl group represented by the general formula (8):

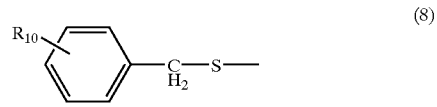

(8)

where $R_{10}$ represents a hydrogen atom, a halogen atom, a CN group, an $NO_2$ group, $COOR_{11}$, $SO_2R_{12}$ ($R_{11}$ represents H, Na, K, $CH_3$, or $C_2H_5$, and $R_{12}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group;

a 2-thienyl group represented by the general formula (9):

(9)

a 2-thienylsulfanyl group represented by the general formula (10):

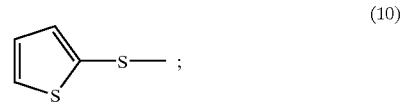

(10)

a 2-thienylcarbonyl group represented by the general formula (11):

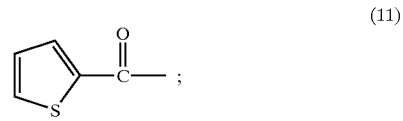

(11)

an unsubstituted or substituted phenylsulfinyl group represented by the general formula (12):

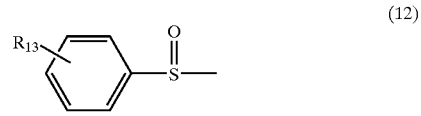

(12)

where $R_{13}$ represents a hydrogen atom, a halogen atom, a CN group, an $NO_2$ group, $COOR_{14}$, $SO_2R_{15}$ ($R_{14}$ represents H, Na, K, $CH_3$, or $C_2H_5$, and $R_{15}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group;

an unsubstituted or substituted phenylsulfonyl group represented by the general formula (13):

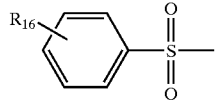

(13)

where $R_{16}$ represents a hydrogen atom, a halogen atom, a CN group, an $NO_2$ group, $COOR_{17}$, $SO_2R_{18}$ ($R_{17}$ represents H, Na, K, $CH_3$, or $C_2H_5$, and $R_{18}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group; and a (phenylmethyl)oxy group represented by the general formula (14):

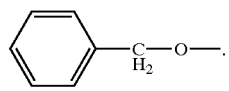

(14)

Further, in the polyhydroxyalkanoate copolymer according to the present invention, it is preferable that the 3-hydroxy-ω-(4-vinylphenyl)-alkanoate unit represented by the general formula (1) is a 3-hydroxy-ω-(4-vinylphenyl)-valerate unit represented by the following formula (15):

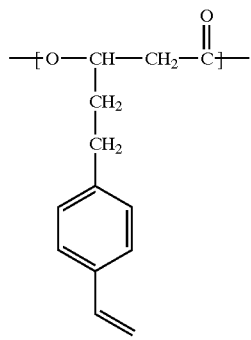

(15)

Further, among the copolymers of the present invention, the copolymer having the number average molecular weight of the polyhydroxyalkanoate copolymer in a range of 2,000 to 1,000,000 is more preferable.

Further, in the method of manufacturing a polyhydroxyalkanoate copolymer according to the present invention which utilizes microorganisms as described above, it is preferable that the $R_{19}$ in the general formulae (17) and (19) is a group selected from the group consisting of:

an unsubstituted or substituted phenyl group represented by the general formula (20):

(20)

where $R_{20}$ represents a hydrogen atom, a halogen atom, a CN group, an $NO_2$ group, a $CH_3$ group, a $C_2H_5$ group, a $C_3H_7$ group, a $CF_3$ group, a $C_2F_5$ group, or a $C_3F_7$ group;

an unsubstituted or substituted phenoxy group represented by the general formula (5);

an unsubstituted or substituted benzoyl group represented by the general formula (6);

an unsubstituted or substituted phenylsulfanyl group represented by the general formula (7);

an unsubstituted or substituted (phenylmethyl)-sulfanyl group represented by the general formula (8);

a 2-thienyl group represented by the general formula (9);

a 2-thienylsulfanyl group represented by the general formula (10);

a 2-thienylcarbonyl group represented by the general formula (11); and a (phenylmethyl)oxy group represented by the formula (14).

The above-described manufacturing method using a microorganism may preferably make use of a method of allowing the microorganism to synthesize the above polyhydroxyalkanoate copolymer by culturing the microorganism in a culture medium containing a raw material consisting of a monomer component.

Furthermore, individually for each of the steps (a) and (b), an oxidizing agent, which can be useful in manufacturing the polyhydroxyalkanoate copolymer having a desired configuration making use of the oxidation of a vinyl group substituted for a phenyl group in the unit represented by the above general formula (1) and/or the oxidation of a sulfanyl group (—S—) provided as a substituent represented by the above general formula (7), may include at least one selected from the group consisting of permanganate, dichromate, periodate, hydrogen peroxide, sodium percarbonate, metachloroperbenzoic acid, performic acid, and peracetic acid.

According to the present invention, in a polyhydroxyalkanoate copolymer, a unit having a side chain with a phenyl group as a structural unit thereof can be incorporated according to a desired molecular design. Therefore, it becomes possible to extremely enlarge the range of applications of the polyhydroxyalkanoate copolymers. For instance, it becomes possible to provide a novel material having biodegradability and ensured processability, or the like.

DETAILED DESCRIPTION OF THE PREFERRED EMBODIMENTS

Figure 1:
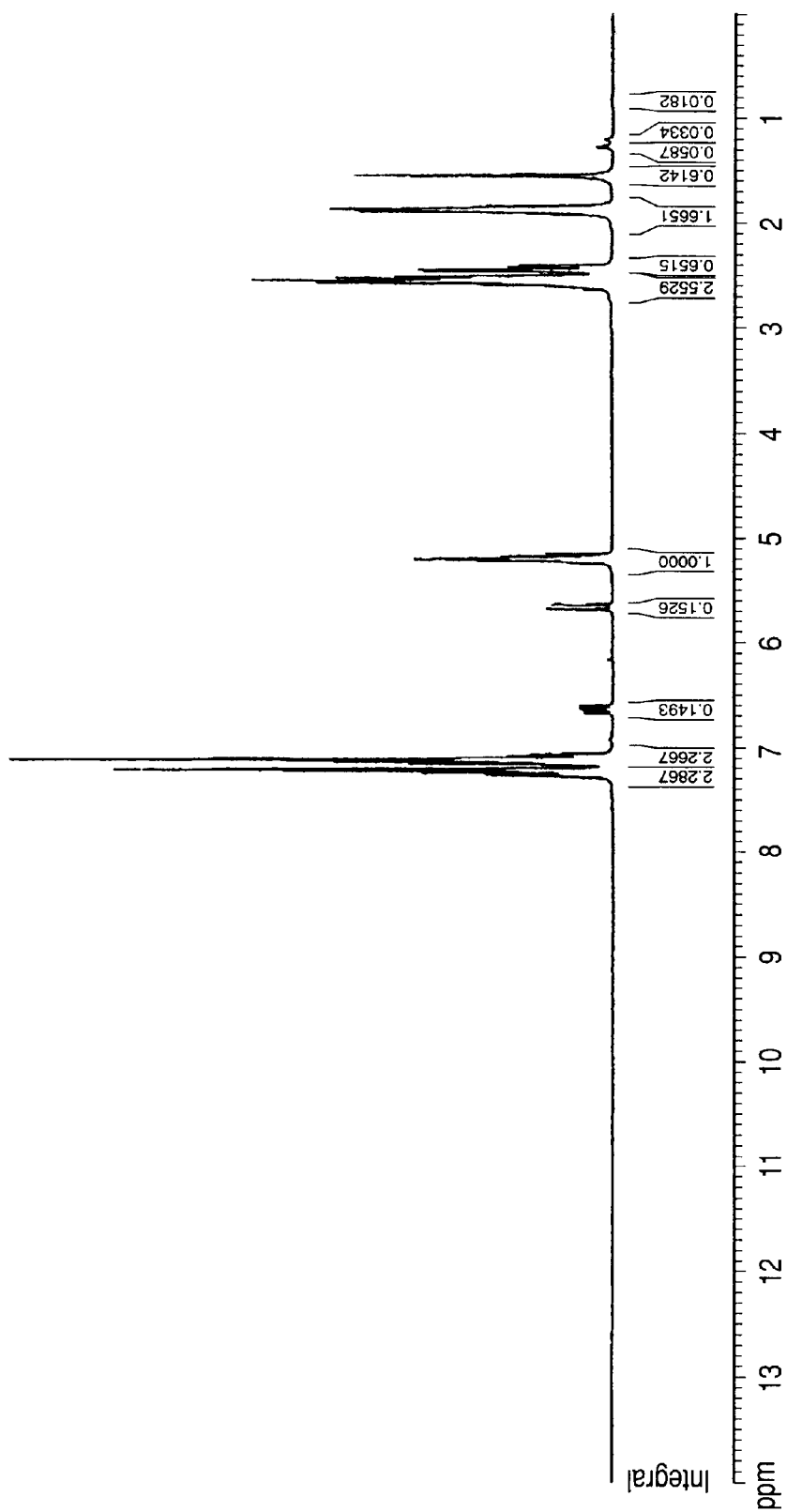
FIG. 1 shows an $^1$H-NMR spectrum of a polyhydroxyalkanoate copolymer obtained in Example 1.
Figure 2:
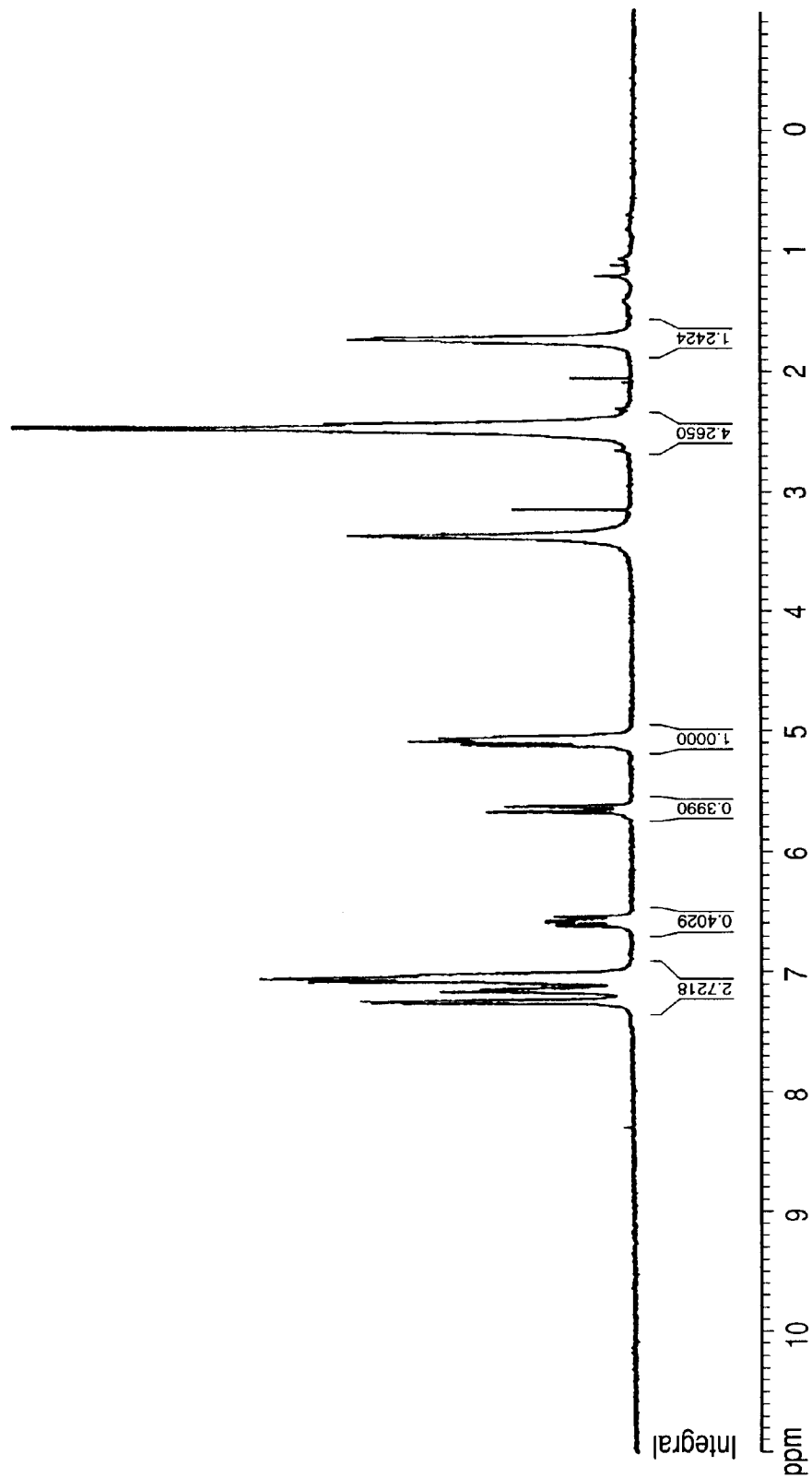
FIG. 2 shows an $^1$H-NMR spectrum of the polyhydroxyalkanoate copolymer obtained in Example 2.

A polyhydroxyalkanoate copolymer of the present invention includes in the same molecule: a 3-hydroxy-ω- substituted alkanoate unit provided as a second structural unit capable of controlling the physical properties such as thermal properties of the polyhydroxyalkanoate copolymer to be obtained, in addition to a 3-hydroxy-ω-(4-vinylphenyl)-alkanoate unit provided as a first structural unit having both of an aromatic ring and a vinyl group on the side chain, where the 3-hydroxy-ω-(4-vinylphenyl)-alkanoate unit is represented by the general formula (1) and includes a 4-vinylphenyl group as a substituent on the end of its side chain, while the 3-hydroxy-ω-substituted alkanoate unit is represented by the general formula (2) or (3) and includes a group as a substituent containing a ring structure selected from a phenyl structure, a thienyl structure, or a cyclohexyl structure as a substituent on the end of its side chain. The presence of two kinds of structural units having ring structures on the ends thereof allows the resulting copolymer to keep characteristics, for example that a glass transition temperature is generally high and good properties as a processed product are achieved due to the aromatic ring, while showing various reactivities derived from the vinyl group. Therefore, the content ratio between the unit component (i) composed of at least one of the 3-hydroxy-ω-(4-vinylphenyl)-alkanoate units represented by the general formula (1) and the unit component (ii) composed of at least one of the 3-hydroxy-ω-substituted alkanoate units represented by the general formulae (2) or (3) can be appropriately selected depending on the selection of the degree to which various reactivities derived from the vinyl group are imparted in addition to the desired characteristics of the copolymer to be obtained (i.e., a high glass transition temperature and good properties as a processed product). Furthermore, other structural units such as a 3-hydroxyalkanoate unit having no ring structure on its side chain may be secondarily contained in addition to the two structural units having ring structures as main components. For instance, the ratio between the unit component (i) and the unit component (ii) may be arbitrarily defined depending on the desired characteristics. Furthermore, under certain circumstances, the polyhydroxyalkanoate copolymer of the present invention may contain a straight-chain 3-hydroxyalkanoate unit having 4 to 12 carbon atoms. In such a case, the percentage of such a unit is preferably 10% by unit or less.

As described above, the polyhydroxyalkanoate copolymer of the present invention may contain a plurality of 3-hydroxy-ω-(4-vinylphenyl)-alkanoate units represented by the general formula (1) having side chains with a single (i.e. uniform) carbon chain length (the value of n) or plural (i.e. different) carbon chain lengths. Similarly, it may contain 3-hydroxy-ω-substituted alkanoate units represented by the general formula (2) or (3) having side chains with a single carbon chain length (the value of m or k) or plural carbon chain lengths. Furthermore, it may contain 3-hydroxy-ω-substituted alkanoate units represented by the general formula (2) or (3) having a ring structure selected in common from a phenyl structure, a thienyl structure, or a cyclohexyl structure as the substituent at the end of a side chain. Alternatively, one unit may contain two or more ring structures having e.g. phenyl structures. Furthermore, the units may contain different ring structures selected among the phenyl, thienyl, and cyclohexyl structures.

The polyhydroxyalkanoate copolymer of the present invention can be available as one produced from a microorganism. In this case, using the microorganism, the structural units are respectively produced from corresponding substrates: a monomer component (A) consisting of at least one ω-(4-vinylphenyl)-alkanoic acid represented by the general formula (16) and a monomer component (B) consisting of at least one of ω-substituted alkanoic acid compounds represented by the general formulae (17) and (18), thereby achieving a copolymer. In the process of producing each structural unit with the microorganism, there is a case that the microorganism produces not only the 3-hydroxy-ω-(4-vinylphenyl)-alkanoate unit and the 3-hydroxy-ω-substituted alkanoate unit having the same number of carbon atoms in the alkanoic acid portion with respect to the corresponding substrates: ω-(4-vinylphenyl)-alkanoic acid represented by the general formula (16) and ω-substituted alkanoic acid compounds represented by the general formulae (17) and (18), but also another unit in which the carbon chain length of each side chain is shortened by two carbon atoms. Therefore, the polyhydroxyalkanoate copolymers in accordance with the present invention include the copolymers containing these related structural units incidentally produced from microorganisms. The polyhydroxyalkanoate copolymer of the present invention produced from the microorganism is produced as an optically active substance as the 3'-carbon atom of each structural unit is an asymmetric carbon atom. Specifically, in the polyhydroxyalkanoate copolymer of the present invention produced from the microorganism, the absolute configuration of the 3'-carbon atom in each structural unit may have the configuration of the R-isomer in any case. Thus, the polyhydroxyalkanoate copolymer of the present invention produced from the microorganism shows its biodegradability based on the above absolute configuration, so that an advantage thereof is a wide range of applications of the novel material in addition to its biocompatibility.

The method of manufacturing a polyhydroalkanoate copolymer in accordance with the present invention utilizes a microorganism to produce a desired copolymer using the monomer components (A) and (B) described above as raw materials thereof. For the production, generally, it is preferable that these raw material components are added into a culture medium and the microorganism to be used is cultured on the culture medium. The culture conditions of the microorganism for the process of manufacturing the polyhydroalkanoate copolymer of the present invention will be described in detail below.

The culture medium for culturing the microorganism is prepared by adding the various required substrate and nutritional elements as described below in an inorganic-salt medium based on a phosphate buffer solution with ammonium salt or nitrate salt.

The content ratio of the substrate to a medium for the production of the desired polyhydroxyalkanoate (i.e., a raw material including the above monomer components (A) and (B)) may be preferably in the range of 0.01% to 1% (w/v), more preferably in the range of 0.02% to 0.2% (w/v) per medium.

Coexistent substrate is added to the medium as a carbon source for the growth of microorganism and an energy supplying source for the production of polyhydroxyalkanoate. In general, the concentration of the coexistent substrate may be preferably in the range of 0.1% to 5% (w/v), more preferably in the range of 0.2% to 2% (w/v) per medium. That is, as a substance to be used as the above coexistent substrate, at least one selected from peptides, yeast extract, organic acids and salts thereof, amino acids and salts thereof, sugars, and straight-chain alkanoic acids having 4 to 12 carbon atoms and salts thereof may be added in the medium. In this case, it is preferable that the addition is performed within a range in which the concentration of the selected substances in total conforms to the above concentration.

For instance, polypeptone may be preferably contained in the medium as one of the above peptides. In addition, the medium may preferably contain yeast extract. As the organic acid and salts, at least one or more organic acids and salts thereof selected from the group consisting of pyruvic acid, oxalacetic acid, citric acid, isocitric acid, ketoglutaric acid, succinic acid, fumaric acid, malic acid, lactic acid, and salts of these organic acids may be preferably used. As the amino acids and the salts thereof, at least one or more amino acids or salts thereof selected from the group consisting of glutamic acid, aspartic acid, and salts of these amino acids may be preferably used. As the sugars, at least one or more sugars selected from the group consisting, for example, of glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose may be preferably used. Furthermore, the media containing the straight-chain alkanoic acids having 4 to 12 carbon atoms or salts thereof may be also used.

In the manufacturing method of the present invention, the medium to be used in the process of culturing the microorganism may be any medium as far as it is an inorganic-salt medium that contains phosphate and a nitrogen source such as ammonium salt, or nitrate. In the process of producing PHA from the microorganism, it is also possible to increase the productivity of PHA by adjusting the concentration of the nitrogen source in the medium.

The microorganism may be cultured at any temperature as far as it is preferable for the growth of its strain to be used. Generally, such a culture temperature may be appropriately in the range of about 15° C. to 37° C., preferably in the range of about 20° C. to 30° C.

Any culture method, such as liquid culture or solid culture, may be applied in the present invention as far as the microorganism can be grown to produce PHA. Furthermore, various kinds of culture methods such as batch culture, fed-batch culture, semi-continuous culture, and continuous culture may be applied in the present invention. As a form of the liquid batch culture, there are several oxygen-supplying methods. For instance, the supply of oxygen is performed by shaking the medium in a shake flask in a shaking incubator or the like, or by stirring the medium for aeration in a jar fermenter.

As a means for allowing the microorganism to produce and accumulate PHA, in addition to the method described above, the productivity of PHA per microorganism may be improved as a whole by transferring the microorganism into a culture where the nitrogen source such as ammonium chloride is restricted after once sufficiently growing the microorganism and then further culturing the microorganism in the presence of a compound to be used as a substrate of the desired structural unit.

Furthermore, in the manufacturing method of the present invention, in addition to the steps of culturing the microorganism under the conditions described above and allowing the microorganism to produce the desired copolymer, an additional step of collecting a polyhydroxyalkanoate copolymer from the cultured microbial cell may be preferably included. In this case, the polyhydroxyalkanoate copolymer is produced from the microorganism, and includes the 3-hydroxy-ω-(4-vinylphenyl)-alkanoate unit represented by the above general formula (1) and the 3-hydroxy-ω-substituted alkanoate unit represented by the above general formula (2) or (3), which are coexisting in the same molecule.

The polyhydroxyalkanoate copolymer of the present invention is generally accumulated in the body of microorganism having the ability of PHA production. As a method of collecting the objective PHA from the microbial cells, any method generally conducted in the art may be applied. For example, the simplest method is a method of extracting PHA using an organic solvent such as chloroform, dichloromethane, or acetone. Instead of the above solvents, dioxane, tetrahydrofuran, acetonitrile, or the like may be used. Under the work environment in which the use of any organic solvent is objectionable, instead of the solvent extraction method, the microbial cells may be chemically broken by the treatment with a surfactant such as SDS, an enzyme such as lysozyme, chemicals such as hypochlorite, ammonia, or EDTA, or may be physically broken by ultrasonic disintegration, homogenization, pressure crushing, bead impact, trituration, grinding, or freeze and thawing method, followed by removing undesired microbial components except for the objective PHA.

The microorganism to be used in the method of manufacturing the copolymer of the present invention is principally one having the ability of PHA production. That is, the desired microorganism may be any microorganism as far as it is capable of producing PHA type polyester that includes a 3-hydroxy-ω-(4-vinylphenyl)-alkanoate unit represented by the general formula (1) when it is cultured in a culture medium containing ω-(4-vinylphenyl) alkanoic acid represented by the general formula (16). Furthermore, it is preferable to select the microorganism having the ability of PHA copolymer production depending on the species of monomer to be used as a raw material.

For instance, the utilizable microorganisms having the ability of PHA production preferably include those belonging to the genus of Pseudomonas. Among them, more preferable strains to be used for the manufacturing method of the present invention are those having the ability of PHA production but having no enzymatic reactivity which causes the vinyl group being substituted on the phenyl group to oxidize or epoxidize it.

More specifically, among the microorganisms belonging to the genus of Pseudomonas, more preferable species to be used in the manufacturing method of the present invention include Pseudomonas cichorii, Pseudomonas putida, Pseudomonas fluorecense, Pseudomonas oleovorans, Pseudomonas aeruginosa, Pseudomonas stutzeri, Pseudomonas jessenii, and so on.

Furthermore, for example, more preferable strains include, Pseudomonas cichorii YN2 strain; FERM BP-7375, Pseudomonas cichorii H45 strain; FERM BP-7374, Pseudomonas jessenii P161 strain; FERM BP-7376, and Pseudomonas putida P91 strain; FERM BP-7373. These four strains are those being deposited to the International Patent Organism Depositary (IPOD), National Institute of Advanced Industrial Science and Technology (AIST), Japan, and also described in Japanese Patent Application Laid-Open No. 2001-288256.

Each of these microorganisms has the ability of using ω-substituted straight-chain alkanoic acid as a raw material in which a six-membered ring atomic group selected from a substituted or unsubstituted phenyl group, a substituted or unsubstituted phenoxy group, and a substituted or unsubstituted cyclohexyl group is substituted at the end of the chain to produce polyhydroxyalkanoate containing a corresponding ω-substituted-3-hydroxy-alkanoate as a monomer unit.

Note that, in the manufacturing method of the present invention, the culture of microorganism, PHA production from the microorganism and accumulation in the microbial body, and the collection of PHA from the microbial body are not limited to the method described above.

As an example of the inorganic-salt culture medium to be used in the manufacturing method of the present invention, the composition of the inorganic-salt culture medium (M9 culture medium) to be used in the examples described below is as follows (per liter of the medium).

| (Composition of M9 culture medium) | |
|---|---|
| $Na_2HPO_4$ | 6.3 g |
| $KH_2PO_4$ | 3.0 g |
| $NH_4Cl$ | 1.0 g |
| NaCl | 0.5 g |
| Water (pH = 7.0) | Remainder |

Furthermore, for attaining a favorable growth of microbial body and the improvement in the productivity of PHA accompanied therewith, there is a need for an addition of an essential trace element such as an essential trace metal element in an appropriate amount to an inorganic-salt culture medium such as M9 culture medium. The addition of a trace component solution having the following composition by about 0.3% (v/v) is substantially effective. The addition of such a-trace component solution supplies a trace metal element or the like to be used for the growth of the microorganism.

| (Composition of trace component solution (per liter)) | |
|---|---|
| Nitrilotriacetic acid | 1.5 g |
| $MgSO_4$ | 3.0 g |
| $MnSO_4$ | 0.5 g |
| NaCl | 1.0 g |
| $FeSO_4$ | 0.1 g |
| $CaCl_2$ | 0.1 g |
| $CoCl_2$ | 0.1 g |
| $ZnSO_4$ | 0.1 g |
| $CuSO_4$ | 0.1 g |
| $AlK(SO_4)_2$ | 0.1 g |
| $H_3BO_3$ | 0.1 g |
| $Na_2MoO_4$ | 0.1 g |
| $NiCl_2$ | 0.1 g |
| Water | Remainder |

In the group represented by the chemical formula (4), a group having a carboxyl group on a benzene ring can be produced by selectively performing an oxidative cleavage on a double bonded portion of a vinyl group substituted for a phenyl group on the end of the side chain in the unit represented by the general formula (1) and a polyhydroxyalkanoate copolymer is obtained in which the group represented by the chemical formula (4) including a group containing a carboxyl group in its benzene ring. At this time, the unit represented by the general formula (1), which is an essential unit component, can remain as it is by preventing all of vinyl groups in the unit represented by the general formula (1) from being oxidized by selecting appropriate reaction conditions.

Such an oxidation reaction can be conducted using an oxidizing agent. Utilizable oxidizing agents include, for example, permanganate, bichromate, periodate, hydrogen peroxide, sodium percarbonate, metachloroperbenzoic acid, ozone, performic acid, and peracetic acid.

Furthermore, as a preferable method for the oxidative cleavage of the carbon-carbon double bond to obtain carboxylic acid using such an oxidizing agent as described above, methods known in the art include, for example, a method using permanganate ("J. Chem. Soc., Perkin. Trans." 1, 806 (1973)), a method using bichromate ("Org. Synth.", 4, 698 (1963)), a method using periodate ("J. Org. Chem.", 46, 19 (1981)), a method using nitric acid (Japanese Patent Application La-d-Open No. 59-190945), and a method using ozone ("J. Am. Chem. Soc.", 81, 4273 (1959)). For polyhydroxyalkanoate, "Macromolecular chemistry", 4, 289–293 (2001) mentioned above describes a method of obtaining a carboxylic acid by initiating the reaction of a carbon-carbon double bond at the end of the side chain in polyhydroxyalkanoate using potassium permanganate as an oxidizing agent under acidic condition. In the present invention, such a method can be available.

In general, potassium permanganate is used as permanganate to be used as an oxidizing agent. Since the oxidative cleavage reaction is a stoichiometric reaction, the usage amount of the permanganate may be typically less than 1 mole equivalent per mole of the unit represented by the chemical formula (1). Considering the efficiency of reaction, alternatively, the usage amount of the permanganate may be also 1 mole equivalent or more.

For setting the reaction system under acidic condition, various kinds of organic and inorganic acids can be generally used. Such acids include sulfuric acid, hydrochloric acid, acetic acid, nitric acid, and so on. However, when the acid of sulfuric acid, nitric acid, hydrochloric acid, or the like is used, a decrease in molecular weight tends to occur because of cleavage of an ester bond of the main chain of polyhydroxyalkanoate. Therefore, it is preferable to use acetic acid. The usage amount of the acid is generally in the range of 0.2 to 200 mole equivalent, preferably in the range of 0.4 to 100 mole equivalent per mole of the unit represented by the chemical formula (1). If it is less than 0.2 mole equivalent, the yield is lowered. If it is higher than 200 mole equivalent, a resolvent is caused as a by-product by the acid. Therefore, both cases are not preferable. Furthermore, for promoting the reaction, crown ether may be used. In this case, the crown ether and the permanganate form a complex, resulting in an effect of increasing the reaction activity. As the crown ether, in general, dibenzo-18-crown-6-ether, dicyclo-18-crown-6-ether, or 18-crown-6-ether is used. It is desired that the usage amount of the crown ether is generally in the range of 1.0 to 2.0 mole equivalent, preferably in the range of 1.0 to 1.5 mole equivalent per mole of permanganate.

A solvent to be used in the oxidative cleavage reaction of the present invention is not specifically limited as far as it is a solvent inactive to the reaction. Utilizable solvents include, for example, water, acetone, ethers such as tetrahydrofuran and dioxane, aromatic hydrocarbons such as benzene, toluene, and xylene, aliphatic hydrocarbons such as hexane and heptane, halogenated hydrocarbons such as methyl chloride, dichloromethane, and chloroform. Among these solvents, considering the solubility of polyhydroxyalkanoate, the halogenated hydrocarbons such as methyl chloride, dichloromethane, and chloroform may be preferably used.

In the above oxidative cleavage reaction of the present invention, the polyhydroxyalkanoate copolymer containing the unit represented by the chemical formula (1), the permanganate, and the acid may be collectively mixed together with the solvent for reaction from the beginning, or successively or intermittently added in a reaction system to initiate the reaction. Alternatively, only the permanganate may be dissolved or suspended in the solvent in advance, followed by successively or intermittently adding the polyhydroxyalkanoate copolymer and the acid into the reaction system to initiate the reaction. Also, only the polyhydroxyalkanoate copolymer may be dissolved or suspended in the solvent in advance, followed by successively or intermittently adding the permanganate or the like into the reaction system to initiate the reaction. Otherwise, only the polyhydroxyalkanoate copolymer and the acid may be dissolved or suspended in the solvent in advance, followed by successively or intermittently adding the permanganate in the reaction system to initiate the reaction. Furthermore, only the permanganate and the acid may be dissolved or suspended into the solvent in advance, followed by successively or intermittently adding the polyhydroxyalkanoate copolymer into the reaction system to initiate the reaction. Furthermore, only the polyhydroxyalkanoate copolymer and the permanganate may be dissolved or suspended in the solvent in advance, followed by successively or intermittently adding the acid in the reaction system to initiate the reaction.

The reaction temperature may be generally in the range of −20° C. to 40° C., preferably 0° C. to 30° C. The reaction time depends on a stoichiometric mixture ratio between the unit represented by the chemical formula (1) and the permanganate and a reaction temperature. In general, however, the reaction time may be 2 to 48 hours.

A polyhydroxyalkanoate copolymer that contains a phenylsulfinyl group represented by the general formula (12) or a phenylsulfonyl group represented by the general formula (13) can be prepared by selectively oxidizing a sulfur portion of a phenylsulfanyl group represented by the general formula (7).

Such an oxidation treatment can be performed by a method using an oxidizing agent selected from the group consisting of permanganate, dichromate, periodate, hydrogen peroxide, sodium percarbonate, metachloroperbenzoic acid, ozone, performic acid, and peracetic acid. As a preferable oxidizing agent, for example, any peroxide compound can be used as far as it contributes to the oxidation of a sulfanyl group (—S—). In the case of considering the efficiency of oxidation, an influence upon the main chain skeleton of polyhydroxyalkanoate, the simplicity of treatment, and so on, in particular, it is preferable to use a peroxide compound selected from the group consisting of hydrogen peroxide, sodium percarbonate, metachloroperbenzoic acid, performic acid, and acetic peracid.

A description will be made first on an oxidation treatment using hydrogen peroxide, which is a simple treating method among them. The easiest treating method using the hydrogen peroxide includes: culturing the microorganisms under the culture conditions described above; suspending the microorganism cells having accumulated thereon a polyhydroxyalkanoate copolymer including the group represented by the general formula (7), which is a polyhydroxyalkanoate copolymer of the present invention, in a hydrogen peroxide solution as it is, followed by treating the microbial bodies by heating and stirring them for a predetermined period of time if required; and collecting the objective polyhydroxyalkanoate copolymer as an insoluble component. If the concentration of the hydrogen peroxide is comparatively high or the reaction temperature is comparatively high, an insoluble component derived from the microbial cells, such as a cell membrane fraction, is oxidized and is then decomposed and solubilized, collecting a polyhydroxyalkanoate copolymer of the present invention in a substantially pure form as an insoluble component. On the other hand, under mild conditions, the insoluble component cannot be sufficiently decomposed and solubilized. In some cases, therefore, the step of fragmenting living cells derived from the microbial cells may partially remain.

In the case of utilizing the mild conditions, it is possible to use a method including: fragmenting cultured microorganism cells in advance; removing an insoluble component derived from the microbial cells; collecting a crude polyhydroxyalkanoate copolymer that contains the group represented by the general formula (7) which is the polyhydroxyalkanoate copolymer of the present invention; and treating the crude copolymer with a hydrogen peroxide solution. Such a method including the steps of previously fragmenting cultured microorganism cells and separating and collecting the polyhydroxyalkanoate copolymer permits the collection of polyhydroxyalkanoate copolymer with a sufficiently high purity even at the time of treatment with a hydrogen peroxide solution under comparatively mild conditions.

In the method of manufacturing the polyhydroxyalkanoate copolymer of the present invention, the step of fragmenting the living cells may be preferably performed by means of ultrasonic disintegration, homogenization, pressure crushing, bead impact, trituration, grinding (cells are ground out in a mortar with an auxiliary agent such as glass powders or alumina powders therein), or freeze and thawing method, without using any chemical for breaking the cell membranes. After the step of fragmenting the living cells, a re-suspended solution of the separated insoluble components is further fractionated into a solid component and a soluble component by means of centrifugal separation or the like. Subsequently, only the solid component that contains a polyhydroxyalkanoate copolymer component is treated with hydrogen peroxide.

Furthermore, as an alternative method of separating a polyhydroxyalkanoate copolymer, there is a method in which only a resulting polyhydroxyalkanoate copolymer is collected by the treatment with hydrogen peroxide after the steps of extraction and isolation. In other words, it is possible to use means for extracting and isolating only a polyhydroxyalkanoate copolymer from microorganism cells in which the polyhydroxyalkanoate copolymer is being accumulated after the culture step using a solvent for the accumulated polyhydroxyalkanoate copolymer, such as chloroform, dichloromethane, or acetone. In the method using such a solvent extraction, the polyhydroxyalkanoate copolymer extracted and collected from microorganism cells tends to aggregate in massive form an aqueous medium where the copolymer is treated with hydrogen peroxide. When the polyhydroxyalkanoate copolymer occurs in massive form, it becomes hindrance to make contact with a peroxide compound such as hydrogen peroxide. In many cases, operational difficulty and complexity are involved, so that for example the efficiency of the oxidizing reaction may remarkably decrease. From this viewpoint, in each of the two methods described above, the polyhydroxyalkanoate copolymer is originally present in finely particulate form in the microorganism cells. While keeping such a state, the finely-powdered polyhydroxyalkanoate copolymer being suspended in water can be subjected to a treatment with hydrogen peroxide. Therefore, the methods can be more easily and efficiently operable.

In the method of manufacturing a polyhydroxyalkanoate copolymer of the present invention, hydrogen peroxide used as an oxidizing agent may be of any form as far as it is able to oxidize a sulfanyl group (—S—). In terms of controlling the manufacturing process, the hydrogen peroxide may be preferably provided as one being dissolved in an aqueous medium, such as a solution containing stable hydrogen peroxide (e.g., an aqueous hydrogen peroxide). For instance, a hydrogen peroxide solution based on JIS K-8230, which can be industrially producible in an enormous quantity in a stable manner, should be recommended. For instance, the aqueous hydrogen peroxide (containing 31% hydrogen peroxide) manufactured by Mitsubishi Gas Chemical Co., Inc., is a preferable hydrogen peroxide solution in the method of the present invention.

In the method of manufacturing a polyhydroxyalkanoate copolymer of the present invention, the conditions for the oxidation treatment with hydrogen peroxide may be varied depending on the state of the polyhydroxyalkanoate copolymer to be treated (e.g., the presence or absence of microbial components, and the occurrence in massive form or finely particulate form). However, the conditions for the oxidation treatment with hydrogen peroxide may be preferably selected almost within the following ranges. In general, when the remaining amount of the microbial component is small or when the polyhydroxyalkanoate copolymer is in finely particulate form, the undesired microbial component can be easily oxidized and solubilized, and the polyhydroxyalkanoate copolymer in finely particulate form itself can be more quickly treated. Therefore, the mild conditions can be applied. At the time of using the aqueous hydrogen peroxide (containing 31% hydrogen peroxide) based on JIS K-8230, the dilution condition (concentration), the usage amount, the treating temperature, the time period of treatment, and so on can be selected within the ranges described below.

The concentration of hydrogen peroxide in the treating solution is in the range of 8% (about four fold dilution) to 31% (undiluted solution), preferably in the range of 16% (about two fold dilutions) to 31% (undiluted solution), depending on the reaction temperature. The reaction amount is, depending on the ratio of the group represented by the general formula (7) contained in the polyhydroxyalkanoate copolymer, in the range of 30 mL to 500 mL, preferably in the range of 100 mL to 300 mL with reference to 1g of the polyhydroxyalkanoate copolymer before the treatment, on the basis of the undiluted aqueous hydrogen peroxide (containing 31% hydrogen peroxide). The reaction temperature is, depending on the concentration of the polyhydroxyalkanoate copolymer in the treatment solution, in the range of 30° C. to 100° C., preferably in the range of 80° C. to 100° C. The reaction time is, depending on the reaction temperature, in the range of 10 to 180 minutes, preferably in the range of 30 to 120 minutes.

In the above ranges of the conditions, the treatment with hydrogen peroxide permits the conversion of a polyhydroxyalkanoate copolymer containing the group represented by the general formula (7) and being accumulated in the body of a microorganism to a polyhydroxyalkanoate copolymer containing a group represented by the general formulae (12) and (13) in its polymer molecule. In this case, the reaction conditions for the hydrogen peroxide treatment are appropriately selected to adjust the reaction rate and reaction amount of oxidation to allow the control of an abundance ratio of each of the groups (7), (12), and (13) to the others.

Next, a description will be made of another method in which metachloroperbenzoic acid (MCPBA) is used as a peroxide compound.

The use of MCPBA allows the oxidation of a sulfanyl group (—S—) being present as a phenylsulfanyl group to proceed stoichiometrically, so that the containing ratio between the groups represented by the general formulae (12) and (13) can be easily controlled. Furthermore, the reaction conditions are mild, so that undesired secondary reactions such as a cleavage of a polyhydroxyalkanoate main chain skeleton and a crosslinking reaction of active portions are hardly occurred. Therefore, in the method of manufacturing a polyhydroxyalkanoate copolymer in accordance with the present invention, metachloroperbenzoic acid (MCPBA) is one of substantially favorable peroxide compounds for manufacturing an objective polyhydroxyalkanoate copolymer with high selectivity.

As the general reaction conditions of the selective oxidation of sulfanyl groups (—S—) to sulfinyl groups (—SO—), a slightly excess amount of MCPBA (i.e., 1.1 to 1.4 moles) per mole of the unit containing the sulfanyl group (—S—) in the polyhydroxyalkanoate copolymer is subjected to a reaction in chloroform at a temperature of 0° C. to 30° C. In the range of these reaction conditions, the oxidation proceeds up to about 90% of theoretical level when the reaction time is set to about 10 hours. In addition, the oxidation can proceed up to almost 100% of theoretical level when the reaction time is set to about 20 hours.

For oxidizing all of the sulfanyl groups (—S—) to sulfonyl groups (—SO$_2$—), slightly more than 2 mol of MCPBA (i.e., 2.1 to 2.4 moles) per mole of the unit containing the sulfanyl group (—S—) in the polyhydroxyalkanoate copolymer may be reacted under the same conditions (the solvent, the reaction temperature, and the reaction time) as described above.

The polyhydroxyalkanoate copolymer to be manufactured by the method of the present invention may include a unit having a carboxyl group or a unit having a sulfinyl structure (—SO—) and a sulfonyl structure (—SO$_2$—) in its polymer molecule. In these structures, there is a possibility that the localization of electrons in the molecule at the end of the unit may be strongly facilitated and the electrical properties thereof may be substantially different from those of the conventional polyhydroxyalkanoate. Such localization of electrons also allows the behavior to the solvent to be different from that of the conventional polyhydroxyalkanoate. For instance, it becomes possible to dissolve the polyhydroxyalkanoate of the present invention in a polar solvent such as dimethylformamide (DMF). In addition, the thermal characteristics can be substantially controlled. In particular, an increase in a glass transition temperature originated from a hydrogen bond is significant. Therefore, it becomes possible to use in a wide range of applications.

Both the above-described two oxidation treatments, i.e., the oxidation treatment on a vinyl group and the oxidation treatment on a sulfanyl group, may be both performed on the same raw material.

Hereinafter, a description will be made of the present invention more specifically with reference to examples thereof. Here, these examples are only provided for illustrating one of preferred embodiments of the present invention. Therefore, the present invention is not limited to the configurations of these examples.

Example 1

A culture medium, which contains 5-(4-vinylphenyl)-valeric acid provided as ω-(4-vinylphenyl)-alkanoic acid represented by the general formula (16), 5-phenyl-valeric acid provided as ω-substituted alkanoic acid represented by the general formula (17), and further, polypeptone provided as peptides, was prepared by the following procedures. 5.0 g of polypeptone (commercially available from Wako Pure Chemical Industries, Ltd.) and 0.9 g of 5-phenyl-valeric acid were dissolved in 1,000 ml of the M9 culture medium and the resultant solution was then charged into a shaking flask (2,000 ml volume), followed by autoclave sterilization. After the heat sterilization, the flask was cooled to room temperature. Furthermore, 0.2 g of 5-(4-vinylphenyl)- valeric acid was added to the flask and the mixture was stirred well. Consequently, a culture medium was prepared.

Previously, a 0.5% polypeptone-containing M9 culture medium was inoculated with a Pseudomonas cichorii YN2 strain and was then shake-cultured at 30° C. for 8 hours. Consequently, a microbial culture solution was prepared. 5 ml of the microbial culture solution was added to the above-mentioned culture medium containing substrates, 5-(4-vinylphenyl)-valeric acid and 5-phenyl-valeric acid. Then, the mixed culture medium was cultured at 30° C. for 40 hours. After the culture, the microbial cells were collected by centrifugation and were then washed with methanol, followed by freeze-drying.

After measuring the dry weight of the microbial cells, chloroform was added. Then, the mixture was stirred at 25° C. for 72 hours to extract polymer accumulated in the microbial cells. The chloroform solution having dissolved therein the extracted polymer was filtrated. The resulting chloroform filtrate was condensed by an evaporator, followed by re-dissolving the polymer in acetone and removing an insoluble fraction by filtration. Subsequently, the filtrate was condensed by the evaporator and was then precipitated and solidified with cold methanol. The solidified precipitate was collected and was dried under reduced pressure. Consequently, the objective polymer was collected. The dry weight of the polymer collected from the above-mentioned collection step was measured.

The structure of the collected polymer was determined using $^1$H-NMR (FT-NMR: Bruker DPX400; $^1$H resonance frequency: 400 MHz; nuclide measured: $^1$H; solvent used: CDCl$_3$; reference: capillary-encapsulated TMS/CDCl$_3$; measuring temperature: room temperature). The collected polymer was found to be a polyhydroxyalkanoate copolymer containing three units represented by the following formula (21) at a content ratio of A:B:C=1:81:18 (% by mole).

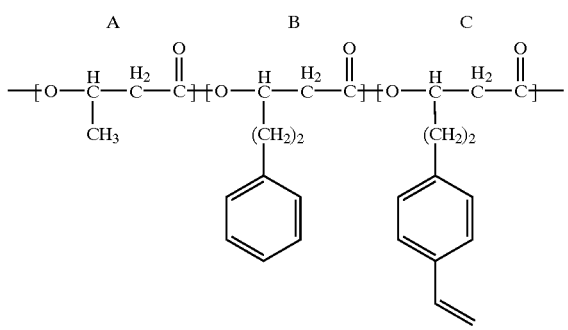

(21)

In addition, the average molecular weight of the polymer was measured using a gel permeation chromatography (trade name: HLC-8220 GPC, commercially available from Tosoh Corporation; column: TSK-Gel Super HM-H, Tosoh Corporation; solvent: chloroform; polymer standard: polystyrene)

In Table 1, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 1

| CDW (mg/L) | PDW (mg/L) | P/C % | Mn (× 10$^4$) | Mw (× 10$^4$) | Mw/Mn |
|---|---|---|---|---|---|
| 873 | 418 | 47.9 | 5.0 | 13.5 | 2.7 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution The glass transition temperature (Tg) of the obtained polymer was measured using a differential scanning calorimeter (trade name: DSC, commercially available from Perkin Elmer Co., Ltd.). The measurement was performed by increasing the temperature from 25° C. to 60° C. at a heating rate of 20° C./minute, decreasing the temperature from 60° C. to −50° C. at a cooling rate of 20° C./minute, and then increasing the temperature again from −50° C. to 200° C. at a heating rate of 20 C./minute. As a result, Tg was observed approximately at a temperature of 17° C. to 20° C.

Example 2

A culture medium, which contains 5-(4-vinylphenyl)-valeric acid provided as ω-(4-vinylphenyl)-alkanoic acid represented by the general formula (16), 5-phenyl-valeric acid provided as ω-substituted alkanoic acid represented by the general formula (17), and further, polypeptone provided as peptides, was prepared by the following procedures. 1.0 g of polypeptone (commercially available from Wako Pure Chemical Industries, Ltd.) and 0.19 g of 5-phenyl-valeric acid were dissolved in 200 ml of the M9 culture medium and the resultant solution was then charged into a shaking flask (500 ml volume), followed by autoclave sterilization. After the heat sterilization, the flask was cooled to room temperature. Furthermore, 0.20 g of 5-(4-vinylphenyl)-valeric acid was added to the flask and the mixture was stirred well. Consequently, a culture medium was prepared.

Previously, a 0.5% polypeptone-containing M9 culture medium was inoculated with a Pseudomonas cichorii YN2 and was then shake-cultured at 30° C. for 8 hours. Consequently, a microbial culture solution was prepared. 1 ml of the microbial culture solution was added to the above-mentioned culture medium containing substrates, 5-(4-vinylpheny)-valeric acid and 5-phenyl-valeric acid. Then, the mixed culture medium was cultured at 30° C. for 40 hours. After the culture, the microbial cells were collected by centrifugation and were then washed with methanol, followed by freeze-drying.

After measuring the dry weight of the microbial cells, chloroform was added. Then, the mixture was stirred at 25° C. for 72 hours to extract polymer accumulated in the microbial cells. The chloroform solution having dissolved therein the extracted polymer was filtrated. The resulting chloroform filtrate was condensed by an evaporator, followed by re-dissolving the polymer in acetone and removing an insoluble fraction by filtration. Subsequently, the filtrate was condensed by the evaporator and was then precipitated and solidified with cold methanol. The solidified precipitate was collected and was dried under reduced pressure. Consequently, the desired polymer was collected. The dry weight of the polymer collected from the above-mentioned collection step was measured.

The structure of the collected polymer was determined using $^1$H-NMR (FT-NMR: Bruker DPX400; $^1$H resonance frequency: 400 MHz; nuclide measured: $^1$H; solvent used: DMSO-d6; reference: capillary-encapsulated TMS/CDCl$_3$; measuring temperature: room temperature). The collected polymer was found to be a polyhydroxyalkanoate copolymer containing two units represented by the following formula (22) at a content ratio of A:B=33:67 (% by mole).

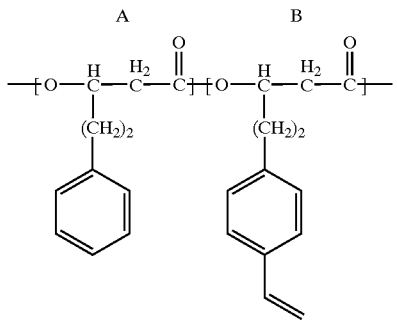

(22)

In addition, the average molecular weight of the polymer was measured by the method using the gel permeation chromatography described in Example 1.

In Table 2, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 2

| CDW (mg/L) | PDW (mg/L) | P/C % | Mn (× 10$^4$) | Mw (× 10$^4$) | Mw/Mn |
|---|---|---|---|---|---|
| 940 | 249 | 26.5 | 3.2 | 10.1 | 3.2 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 3

In this example, the production of polymer was performed by the same steps under the same conditions as those of Example 1, except that the strain P161 was used as the microorganism instead of the YN2 strain used in Example 1.

The structure of the collected polymer was determined by $^1$H-NMR measurement just as in the case with Example 1. The collected polymer was found to be a polyhydroxyalkanoate copolymer containing three units represented by the following formula (23) at a content ratio of A:B:C=2:78:20 (% by mole).

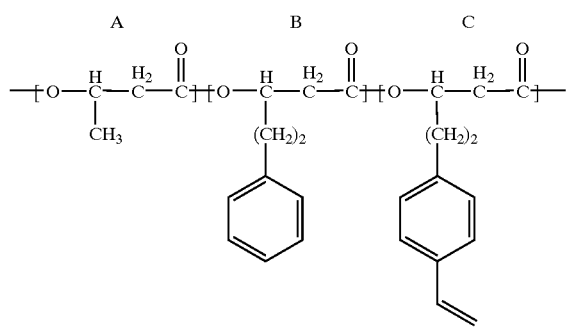

(23)

In addition, the average molecular weight of the polymer was measured by the method using the gel permeation chromatography described in Example 1.

In Table 3, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 3

| CDW (mg/L) | PDW (mg/L) | P/C % | Mn (× 10$^4$) | Mw (× 10$^4$) | Mw/Mn |
|---|---|---|---|---|---|
| 708 | 288 | 40.7 | 3.6 | 8.2 | 2.3 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 4

In this example, the production of polymer was performed by the same steps under the same conditions as those of Example 1, except that the H45 strain was used as the microorganism instead of the YN2 strain used in Example 1.

The structure of the collected polymer was determined by $^1$H-NMR measurement just as in the case with Example 1. The collected polymer was found to be a polyhydroxyalkanoate copolymer containing three units represented by the following formula (24) at a content ratio of A:B:C=1:82:17 (% by mole).

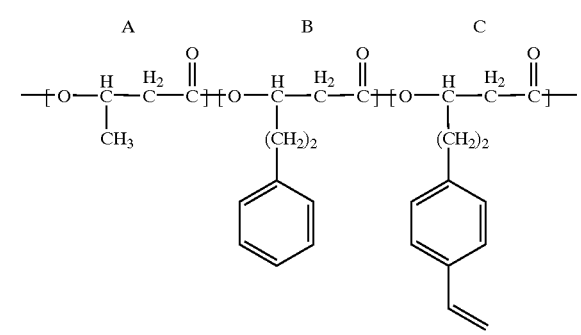

(24)

In addition, the average molecular weight of the polymer was measured by the method using the gel permeation chromatography described in Example 1.

In Table 4, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 4

| CDW (mg/L) | PDW (mg/L) | P/C % | Mn (× 10$^4$) | Mw (× 10$^4$) | Mw/Mn |
|---|---|---|---|---|---|
| 669 | 211 | 31.5 | 4.2 | 9.9 | 2.4 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 5

In this example, the production of polymer was performed by the same steps under the same conditions as those of Example 1, except that the H45 strain was used as the microorganism instead of the YN2 strain used in Example 1, and that 5.0 g of yeast extract (trademark: BACTO, manufactured by Difco Ltd.) was added instead of polypeptone to a culture medium.

The structure of the collected polymer was determined by $^1$H-NMR measurement just as in the case with Example 1. The collected polymer was found to be a polyhydroxyalkanoate copolymer containing two units represented by the following formula (25) at a content ratio of A:B=81:19 (% by mole).

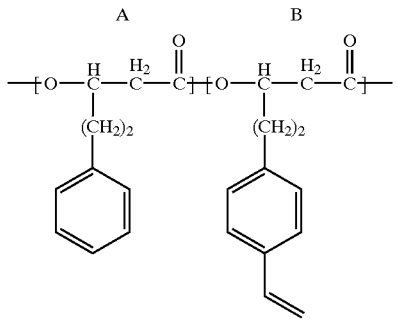

(25)

In addition, the average molecular weight of the polymer was measured by the method using the gel permeation chromatography described in Example 1.

In Table 5, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 5

| CDW (mg/L) | PDW (mg/L) | P/C % | Mn (× 10$^4$) | Mw × 10$^4$ | Mw/Mn |
|---|---|---|---|---|---|
| 462 | 132 | 28.6 | 5.1 | 11.3 | 2.2 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 6

In this example, the production of polymer was performed by the same steps under the same conditions as those of Example 1, except that 5.0 g of D-glucose was added to a culture medium instead of polypeptone added thereto in Example 1.

The structure of the collected polymer was determined by $^1$H-NMR measurement just as in the case with Example 1. The collected polymer was found to be a polyhydroxyalkanoate copolymer containing three units represented by the following formula (26) at a content ratio of A:B:C=1:79:20 (% by mole).

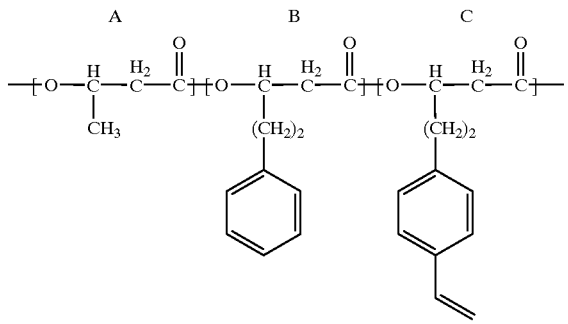

(26)

In addition, the average molecular weight of the polymer was measured by the method using the gel permeation chromatography described in Example 1.

In Table 6, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 6

| CDW (mg/L) | PDW (mg/L) | P/C % | Mn (× 10$^4$) | Mw (× 10$^4$) | Mw/Mn |
|---|---|---|---|---|---|
| 796 | 401 | 50.4 | 5.1 | 12.9 | 2.5 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 7

In this example, the production of polymer was performed by the same steps under the same conditions as those of Example 1, except that 5.0 g of sodium pyruvate that is water-soluble salt of organic acid was added to a culture medium instead of polypeptone added thereto in Example 1.

The structure of the collected polymer was determined by $^1$H-NMR measurement just as in the case with Example 1. The collected polymer was found to be a polyhydroxyalkanoate copolymer containing three units represented by the following formula (27) at a content ratio of A:B:C=2:79:19 (% by mole).

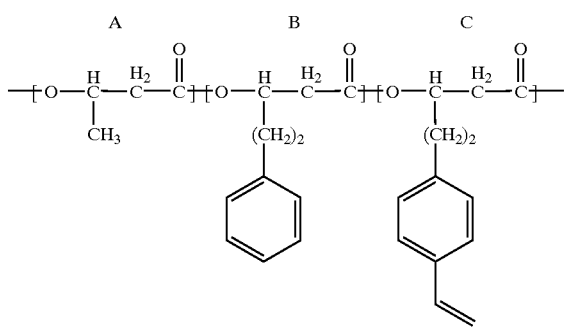

(27)

In addition, the average molecular weight of the polymer was measured by the method using the gel permeation chromatography described in Example 1.

In Table 7, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 7

| CDW (mg/L) | PDW (mg/L) | P/C % | Mn ($\times 10^4$) $\times 10^4$ | Mw ($\times 10^4$) $\times 10^4$ | Mw/Mn |
|---|---|---|---|---|---|
| 822 | 412 | 50.1 | 4.9 | 13.0 | 2.7 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 8

In this example, the production of polymer was performed by the same steps under the same conditions as those of Example 1, except that 5.0 g of sodium glutamate that is water-soluble salt of amino acid was added to a culture medium instead of polypeptone added thereto in Example 1.

The structure of the collected polymer was determined by $^1$H-NMR measurement just as in the case with Example 1. The collected polymer was found to be a polyhydroxyalkanoate copolymer containing three units represented by the following formula (28) at a content ratio of A:B:C=1:83:16 (% by mole).

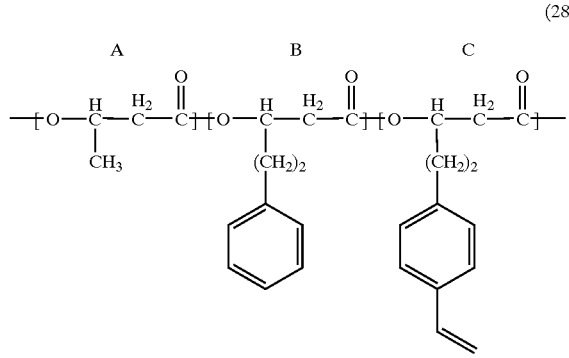

(28)

In addition, the average molecular weight of the polymer was measured by the method using the gel permeation chromatography described in Example 1.

In Table 8, the dry weight of the microbial cells obtained though the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 8

| CDW (mg/L) | PDW (mg/L) | P/C % | Mn ($\times 10^4$) $\times 10^4$ | Mw ($\times 10^4$) $\times 10^4$ | Mw/Mn |
|---|---|---|---|---|---|
| 776 | 389 | 50.1 | 5.0 | 12.2 | 2.4 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 9

A culture medium, which contains 5-(4-vinylphenyl)-valeric acid provided as ω-(4-vinylphenyl)-alkanoic acid represented by the general formula (16), 5-phenoxy-valeric acid provided as ω-substituted alkanoic acid represented by the general formula (17), and further, polypeptone provided as peptides, was prepared by the following procedures. 5.0 g of polypeptone (commercially available from Wako Pure Chemical Industries, Ltd.), 0.21 g of 5-(4-vinylphenyl)-valeric acid, and 1.16 g of 5-phenoxy-valeric acid were dissolved in 1,000 ml of the M9 culture medium and the resultant solution was then charged into a shaking flask (2,000 ml volume), followed by subjecting to autoclave sterilization. After the heat sterilization, the flask was cooled to room temperature. Consequently, a culture medium was prepared.

Previously, a 0.5% polypeptone-containing M9 culture medium was inoculated with Pseudomonas cichorii YN2 and was then shake-cultured at 30° C. for 8 hours. Consequently, a microbial culture solution was prepared. 10 ml of the microbial culture solution was added to the above culture medium containing substrates, 5-(4-vinylphenyl)-valeric acid and 5-phenoxy-valeric acid. Then, the mixed culture medium was cultured at 30° C. for 40 hours. After the culture, the microbial cells were collected by centrifugation and were then washed with methanol, followed by freeze-drying.

After measuring the dry weight of the microbial cells, chloroform was added. Then, the mixture was stirred at 35° C. for 17 hours to extract polymer accumulated in the microbial cells. The chloroform solution having dissolved therein the extracted polymer was filtrated. The resulting chloroform filtrate was condensed by an evaporator, followed by re-dissolving the polymer in acetone and removing an insoluble fraction by filtration. Subsequently, the filtrate was condensed by the evaporator and was then precipitated and solidified with cold methanol. The solidified precipitate was collected and was dried under reduced pressure. Consequently, the objective polymer was collected. The dry weight of the polymer collected from the above collection step was measured.

Figure 3:
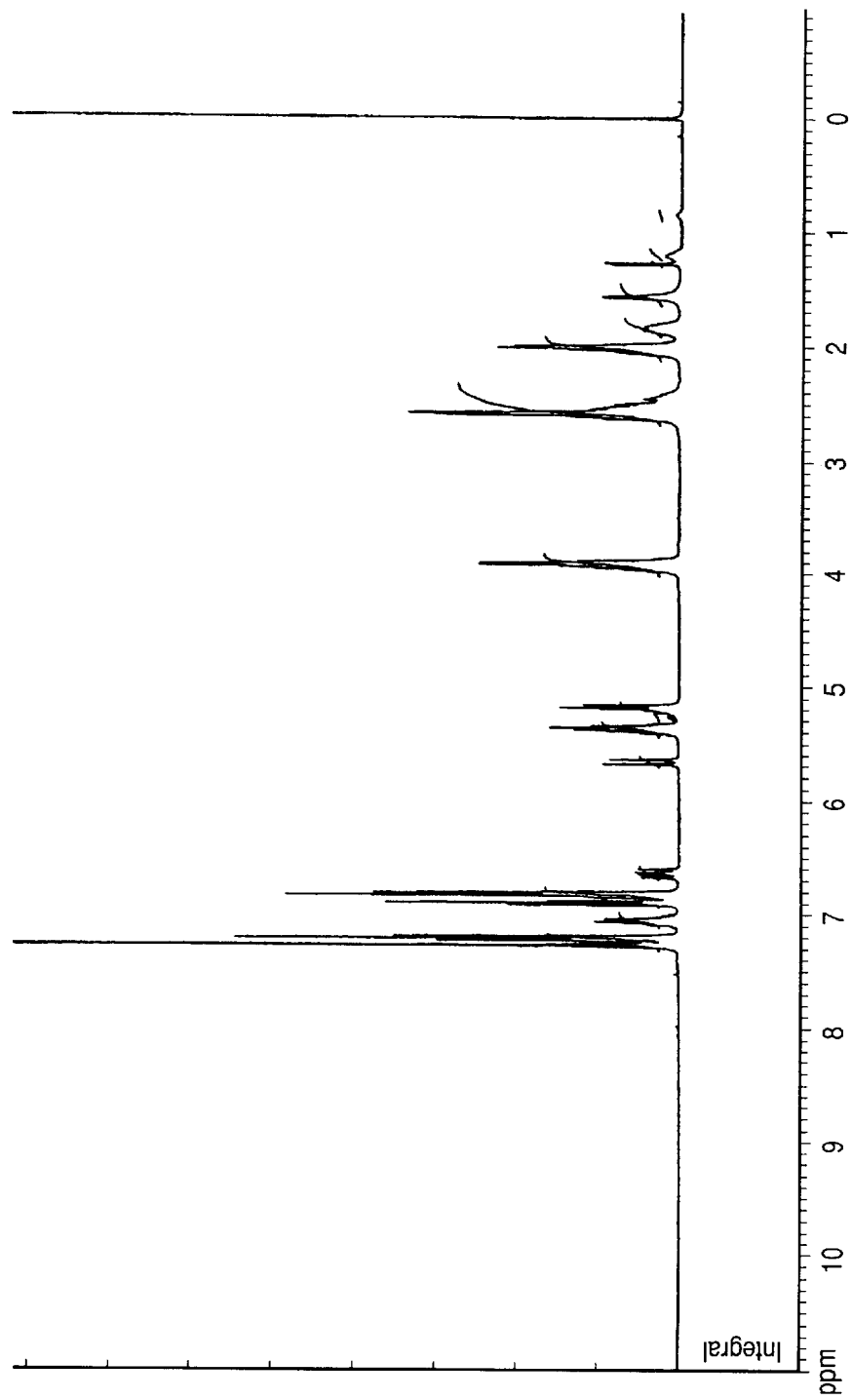
FIG. 3 shows an $^1$H-NMR spectrum of the polyhydroxyalkanoate copolymer obtained in Example 9.

The structure of the collected polymer was determined using $^1$H-NMR (FT-NMR: Bruker DPX400; $^1$H resonance frequency: 400 MHz; nuclide measured: $^1$H; solvent used: CDCl$_3$; reference: capillary-encapsulated TMS/CDCl$_3$; measuring temperature: room temperature). $^1$H-NMR spectrum thereof is shown in FIG. 3. As a result, the collected polymer was found to be a polyhydroxyalkanoate copolymer containing three units represented by the following formula (29) at a content ratio of D:E:F=8:69:23 (% by mole).

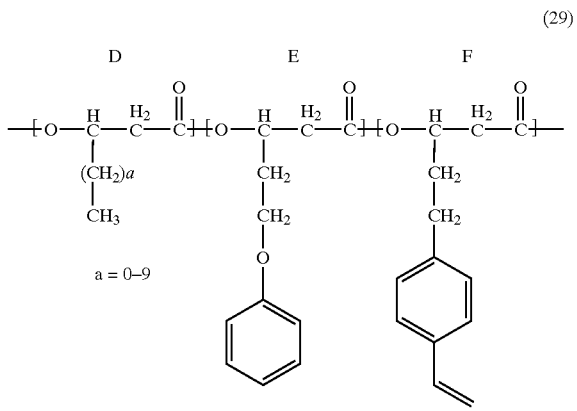

(29)

In Table 9, the dry weight of the microbial cells obtained through the above-mentioned steps, the dry weight of the collected polymer, and the weight ratio of the collected polymer per dried microbial cell are listed together.

TABLE 9

| CDW (mg/L) | PDW (mg/L) | P/C % |
|---|---|---|
| 590 | 192 | 32.5 |

CDW: dry weight of microbial cells
PDW: dry weight of polymer
P/C: dry weight of polymer/dry weight of microbial cells Example 10

A culture medium, which contains 5-(4-vinylphenyl)-valeric acid provided as ω-(4-vinylphenyl)-alkanoic acid represented by the general formula (16), 5-(phenylsulfanyl)-valeric acid provided as ω-substituted alkanoic acid represented by the general formula (17), and further, polypeptone provided as peptides, was prepared by the following procedures. 5.0 g of polypeptone (commercially available from Wako Pure Chemical Industries, Ltd.), 0.21 g of 5-(4-vinylphenyl)-valeric acid and 1.28 g of 5-(phenylsulfanyl)-valeric acid were dissolved in 1,000 ml of the M9 culture medium and the resultant solution was then charged into a shaking flask (2,000 ml volume), followed by autoclave sterilization. After the heat sterilization, the flask was cooled to room temperature to prepare the culture medium.

Previously, a 0.5% polypeptone-containing M9 culture medium was inoculated with a Pseudomonas cichorii YN2 strain and was then shake-cultured at 30° C. for 8 hours. Consequently, a microbial culture solution was prepared. 10 ml of the microbial culture solution was added to the above culture medium containing substrates, 5-(4-vinylpheny) valerianic acid and 5-(phenylsulfanyl)-valeric acid. Then, the mixed culture medium was cultured at 30° C. for 38 hours. After the culture, the microbial cells were collected by centrifugation and were then washed with methanol, followed by freeze-drying.

After measuring the dry weight of the microbial cells, chloroform was added. Then, the mixture was stirred at 35° C. for 17 hours to extract polymer accumulated in the microbial cells. The chloroform solution having dissolved therein the extracted polymer was filtrated. The resulting chloroform filtrate was condensed by an evaporator, followed by re-dissolving the polymer in acetone and removing an insoluble fraction by filtration. Subsequently, the filtrate was condensed by the evaporator and was then precipitated and solidified with cold methanol. The solidified precipitate was collected and was dried under reduced pressure. Consequently, the objective polymer was collected. The dry weight of the polymer collected from the above collection step was measured.

Figure 4:
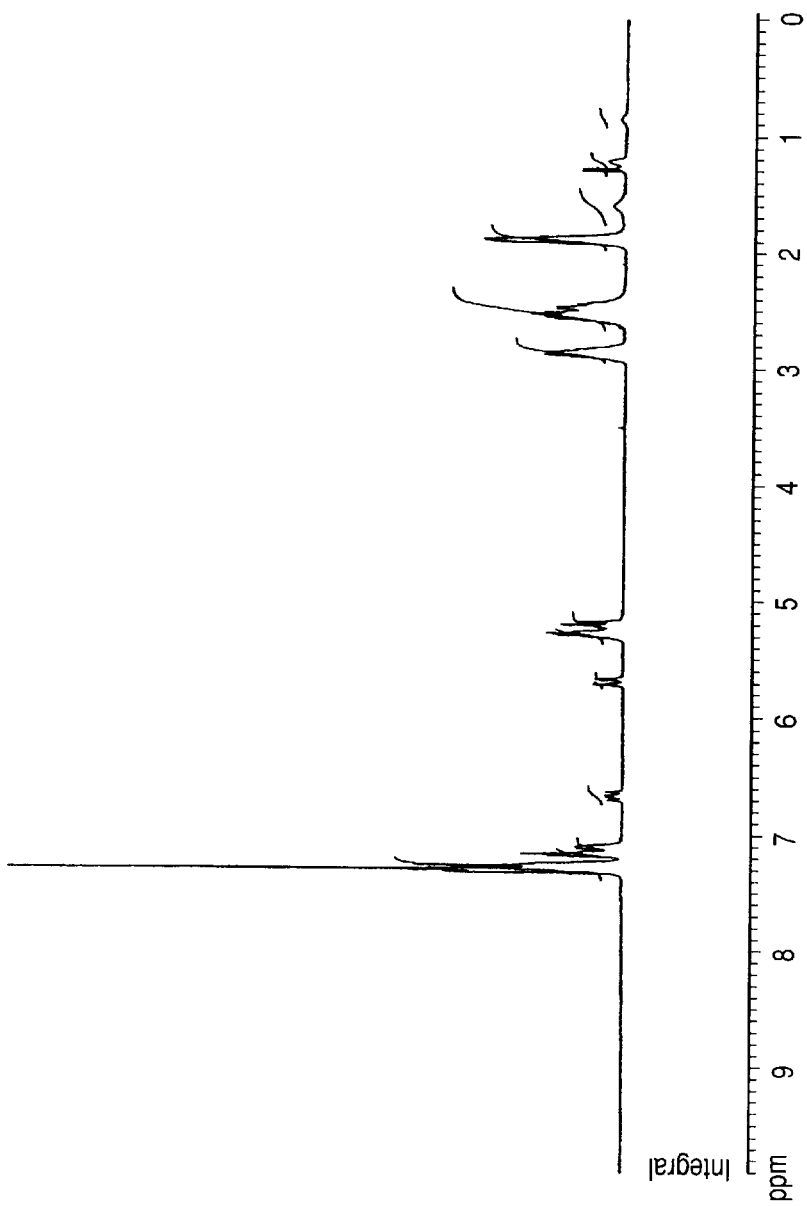
FIG. 4 shows an $^1$H-NMR spectrum of the polyhydroxyalkanoate copolymer obtained in Example 10.

The structure of the collected polymer was determined using $^1$H-NMR (FT-NMR: Bruker DPX400; $^1$H resonance frequency: 400 MHz; nuclide measured: $^1$H; solvent used: $CDCl_3$; reference: capillary-encapsulated $TMS/CDCl_3$; measuring temperature: room temperature). $^1$H-NMR spectrum thereof is shown in FIG. 4. As a result, the collected polymer was found to be a polyhydroxyalkanoate copolymer containing three units represented by the following formula (30) at a content ratio of G:H:I=10:70:20 (% by mole).

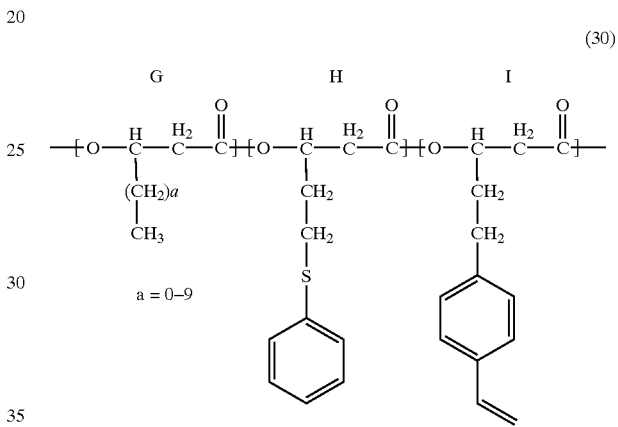

(30)

In addition, the average molecular weight of the polymer was measured using a gel permeation chromatography (trade name: HLC-8220 GPC, commercially available from Tosoh Corporation; column: TSK-Gel Super HM-H, Tosoh Corporation; solvent: chloroform; polymer standard: polystyrene)

In Table 10, the dry weight of the microbial cells obtained though the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 10

| CDW (mg/L) | PDW (mg/L) | P/C % | Mn (×10$^4$) | Mw (×10$^4$) | Mw/Mn |
|---|---|---|---|---|---|
| 917 | 369 | 40.2 | 4.8 | 12.3 | 2.5 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution The glass transition temperature (Tg) of the obtained polymer was measured using a differential scanning calorimeter (trade name: Pyris 1, commercially available from Perkin Elmer Co., Ltd.). The measurement was performed by increasing the temperature from −50° C. to 200° C. at a heating rate of 20° C./minute, decreasing the temperature from 200° C. to −50° C. at a cooling rate of 20° C./minute, and then increasing the temperature again from −50° C. to 200° C. at a heating rate of 20° C./minute. As a result, Tg was observed approximately at a temperature of 8° C.

Example 11

A culture medium, which contains 5-(4-vinylphenyl)-valeric acid provided as ω-(4-vinylphenyl)-alkanoic acid represented by the general formula (16), 4-cyclohexyl-butyric acid provided as ω-substituted alkanoic acid represented by the general formula (18), and further, polypeptone provided as peptides, was prepared by the following procedures. 1.0 g of polypeptone (commercially available from Wako Pure Chemical Industries, Ltd.), 0.041 g of 5-(4-vinylphenyl)-valeric acid, and 0.204 g of 4-cyclohexyl-butyric acid were dissolved in 200 ml of the M9 culture medium and the resultant solution was then charged into a shaking flask (500 ml volume), followed by autoclave sterilization. After the heat sterilization, the flask was cooled to room temperature. Consequently, a culture medium was prepared.

The above culture medium containing substrates, 5-(4-vinylpheny)-valeric acid and 4-cyclohexyl-butyric acid was inoculated with a Pseudomonas cichorii YN2 strain. Then, the mixed culture medium was cultured at 30° C. for 41 hours. After the culture, the microbial cells were collected by centrifugation and were then washed with methanol, followed by freeze-drying.

After weighing the dry weight of the microbial cells, 20 ml of chloroform was added. Then, the mixture was stirred at 35° C. for 15 hours to extract polymer accumulated in the microbial cells. The chloroform solution having dissolved therein the extracted polymer was filtrated. The resulting chloroform filtrate was condensed by an evaporator. Subsequently, the filtrate was precipitated and solidified with cold methanol. The solidified precipitate was collected and was dried under reduced pressure. Consequently, the objective polymer was collected. The dry weight of the polymer collected from the above collection step was measured.

Figure 5:
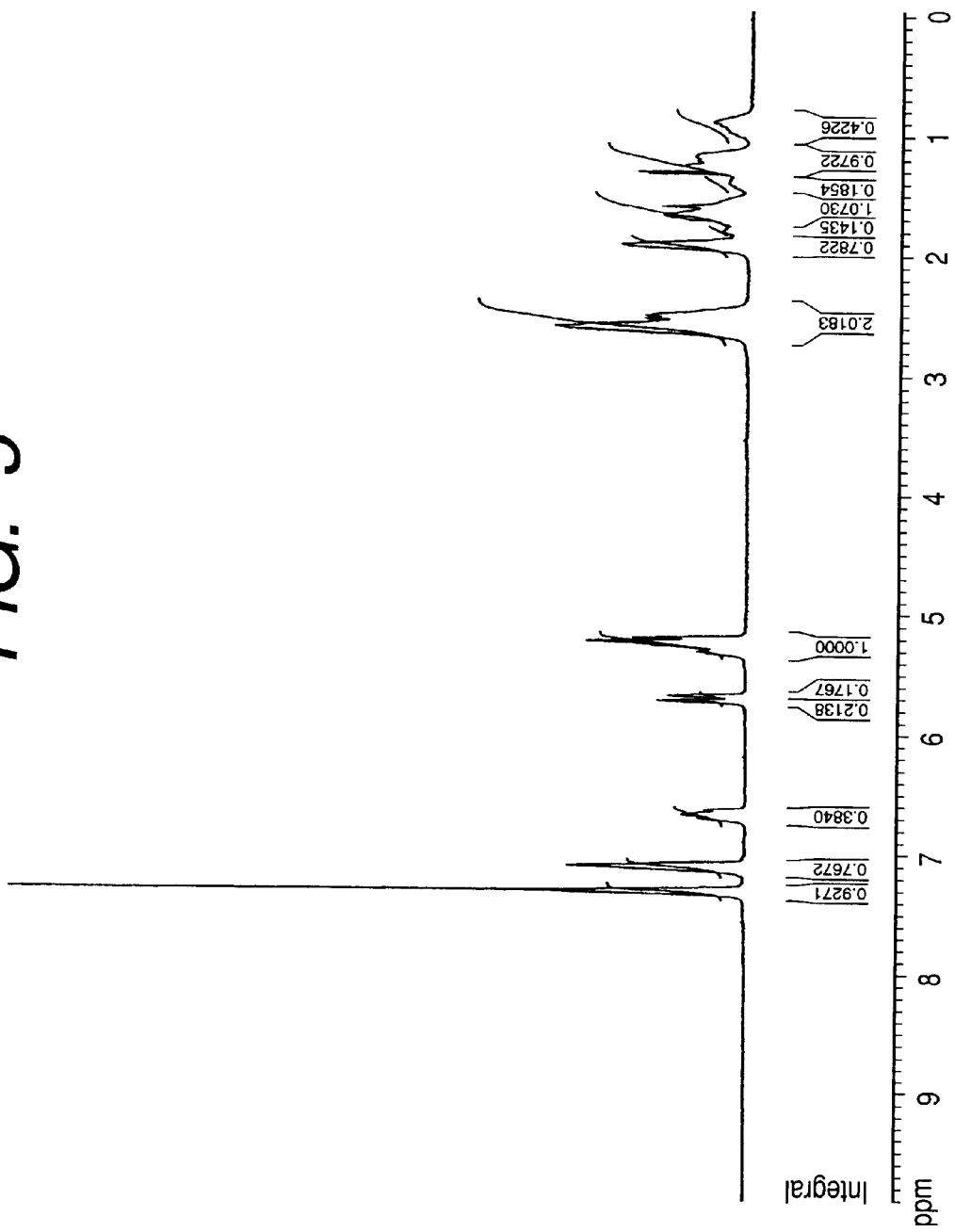
FIG. 5 shows an $^1$H-NMR spectrum of the polyhydroxyalkanoate copolymer obtained in Example 11.

The structure of the collected polymer was determined using $^1$H-NMR (FT-NMR: Bruker DPX400; $^1$H resonance frequency: 400 MHz; nuclide measured: $^1$H; solvent used: $CDCl_3$; reference: capillary-encapsulated $TMS/CDCl_3$; measuring temperature: room temperature). $^1$H-NMR spectrum thereof is shown in FIG. 5. As a result, the collected polymer was found to be a polyhydroxyalkanoate copolymer containing three units represented by the following formula (31) at a content ratio of J:K=37:63 (% by mole).

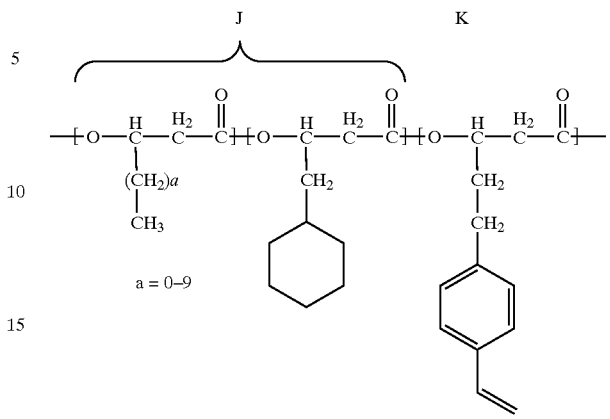

In addition, the average molecular weight of the polymer was measured using a gel permeation chromatography (trade name: HLC-8220 GPC, commercially available from Tosoh Corporation; column: TSK-Gel Super HM-H, Tosoh Corporation; solvent: chloroform; polymer standard: polystyrene) In Table 11, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 11

| CDW (mg/L) | PDW (mg/L) | P/C % | Mn (×10$^4$) | Mw (×10$^4$) | Mw/Mn |
|---|---|---|---|---|---|
| 724 | 159 | 22.0 | 5.4 | 12.3 | 2.3 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 12

A culture medium, which contains 5-(4-vinylphenyl)-valeric acid provided as ω-(4-vinylphenyl)-alkanoic acid represented by the general formula (16), 5-benzoyl-valeric acid provided as ω-substituted alkanoic acid represented by the general formula (17), and further, polypeptone provided as peptides, was prepared by the following procedures. 1.0 g of polypeptone (commercially available from Wako Pure Chemical Industries, Ltd.), 0.041 g of 5-(4-vinylphenyl)-valeric acid, and 0.247 g of 5-benzoyl-valeric acid were dissolved in 200 ml of the M9 culture medium and the resultant solution was then charged into a shaking flask (500 ml volume), followed by autoclave sterilization. After the heat sterilization, the flask was cooled to room temperature. Consequently, a culture medium was prepared.

The above culture medium containing substrates, 5-(4-vinylpheny)-valeric acid and 5-benzoyl-valeric acid was inoculated with a Pseudomonas cichorii YN2 strain. Then, the mixed culture medium was cultured at 30° C. for 41 hours. After the culture, the microbial cells were collected by centrifugation and were then washed with methanol, followed by freeze-drying.

After measuring the dry weight of the microbial cells, 20 ml of chloroform was added. Then, the mixture was stirred at 35° C. for 15 hours to extract polymer accumulated in the microbial cells. The chloroform solution having dissolved therein the extracted polymer was filtrated. The resulting chloroform filtrate was condensed by an evaporator. Subsequently, the filtrate was precipitated and solidified with cold methanol. The solidified precipitate was collected and was dried under reduced pressure. Consequently, the objective polymer was collected. The dry weight of the polymer collected from the above collection step was measured.

Figure 6:
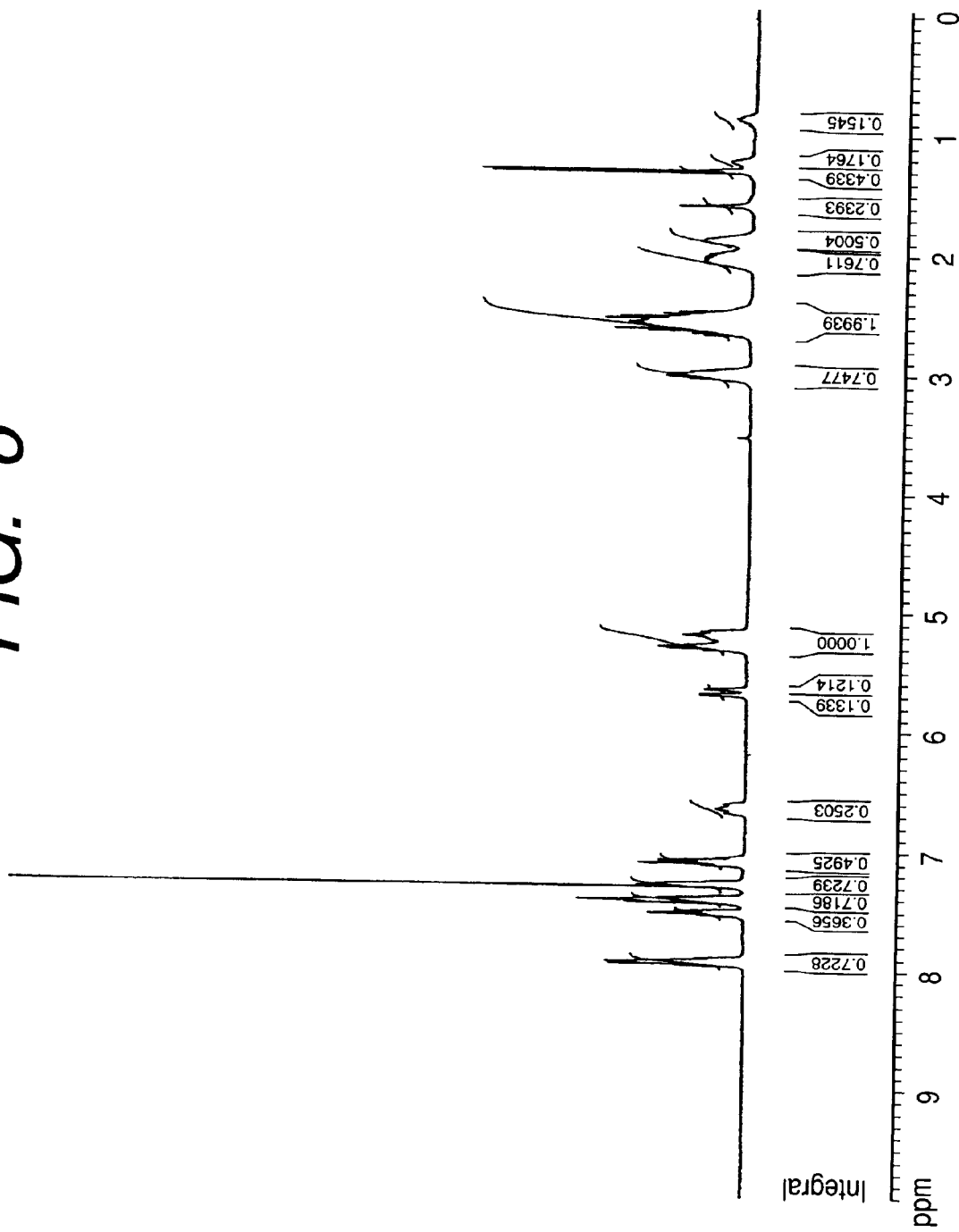
FIG. 6 shows an $^1$H-NMR spectrum of the polyhydroxyalkanoate copolymer obtained in Example 12.

The structure of the collected polymer was determined using $^1$H-NMR (FT-NMR: Bruker DPX400; $^1$H resonance frequency: 400 MHz; nuclide measured: $^1$H; solvent used: $CDCl_3$; reference: capillary-encapsulated $TMS/CDCl_3$; measuring temperature: room temperature). $^1$H-NMR spectrum thereof is shown in FIG. 6. As a result, the collected polymer was found to be a polyhydroxyalkanoate copolymer containing three units represented by the following formula (32) at a content ratio of L:M:N=18:48:34 (% by mole).

(32)

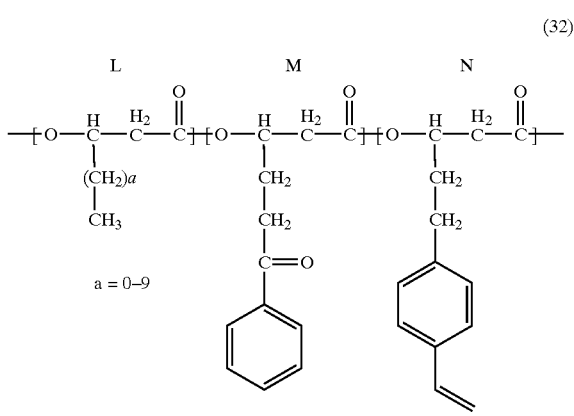

In addition, the average molecular weight of the polymer was measured using a gel permeation chromatography (trade name: HLC-8220 GPC, commercially available from Tosoh Corporation; column: TSK-Gel Super HM-H, Tosoh Corporation; solvent: chloroform; polymer standard: polystyrene).

In Table 12, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 12

| CDW (mg/L) | PDW (mg/L) | P/C % | Mn (×10$^4$) | Mw (×10$^4$) | Mw/Mn |
|---|---|---|---|---|---|
| 726 | 208 | 28.7 | 11.0 | 36.3 | 3.3 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution Example 13

A culture medium, which contains 5-(4-vinylphenyl)-valeric acid provided as ω-(4-vinylphenyl)-alkanoic acid represented by the general formula (16), 5-(2-thienyl)-valeric acid provided as ω-substituted alkanoic acid represented by the general formula (17), and further, polypeptone provided as peptides, was prepared by the following procedures. 1.0 g of polypeptone (commercially available from Wako Pure Chemical Industries, Ltd.), 0.041 g of 5-(4-vinylphenyl)-valeric acid, and 0.221 g of 5-(2-thienyl)-valeric acid were dissolved in 200 ml of the M9 culture medium and the resultant solution was then charged into a shaking flask (500 ml volume), followed by autoclave sterilization. After the heat sterilization, the flask was cooled to room temperature. Consequently, a culture medium was prepared.

The above culture medium containing substrates, 5-(4-vinylpheny)-valeric acid and 5-(2-thienyl)-valeric acid was inoculated with a Pseudomonas cichorii YN2 strain. Then, the mixed culture medium was incubated at 30° C. for 41 hours. After the culture, the microbial cells were collected by centrifugation and were then washed with methanol, followed by freeze-drying.

After weighing the dry weight of the microbial cells, 20 ml of chloroform was added. Then, the mixture was stirred at 35° C. for 15 hours to extract polymer accumulated in the microbial cells. The chloroform solution having dissolved therein the extracted polymer was filtrated. The resulting chloroform filtrate was condensed by an evaporator, and was then precipitated and solidified with cold methanol. The solidified precipitate was collected and was dried under reduced pressure. Consequently, the desired polymer was collected. The dry weight of the polymer collected from the above collection step was measured.

Figure 7:
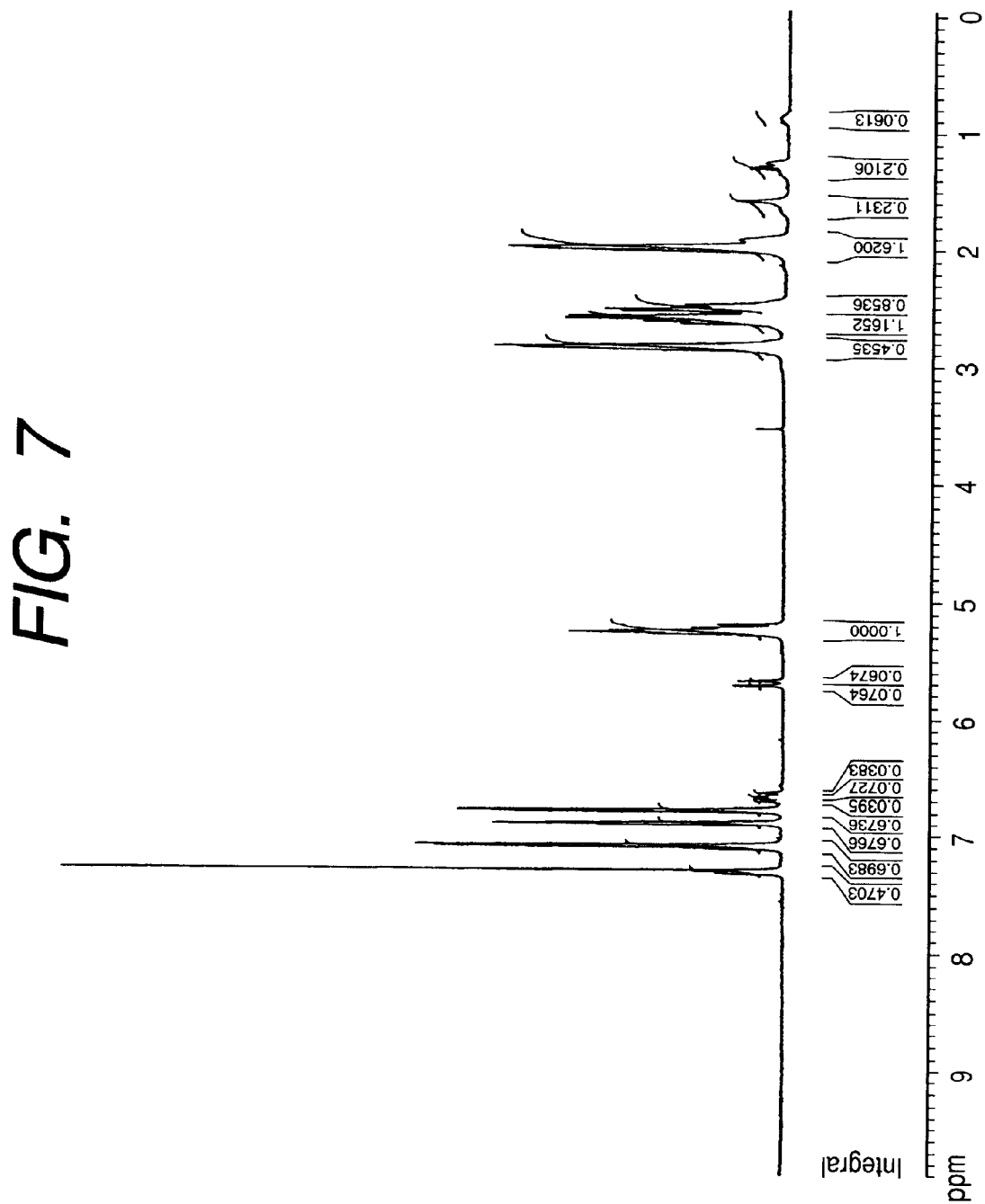
FIG. 7 shows an $^1$H-NMR spectrum of the polyhydroxyalkanoate copolymer obtained in Example 13.

The structure of the collected polymer was determined using $^1$H-NMR (FT-NMR: Bruker DPX400; $^1$H resonance frequency: 400 MHz; nuclide measured: $^1$H; solvent used: $CDCl_3$; reference: capillary-encapsulated $TMS/CDCl_3$; measuring temperature: room temperature). $^1$H-NMR spectrum thereof is shown in FIG. 7. As a result, the collected polymer was found to be a polyhydroxyalkanoate copolymer containing three units represented by the following formula (33) at a content ratio of O:P:Q=4:79:17 (% by mole).

(33)

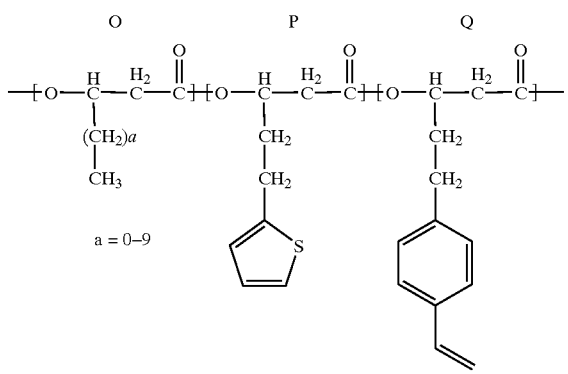

In addition, the average molecular weight of the polymer was measured using a gel permeation chromatography (trade name: HLC-8220 GPC, commercially available from Tosoh Corporation; column: TSK-Gel Super HM-H, Tosoh Corporation; solvent: chloroform; polymer standard: polystyrene)

In Table 13, the dry weight of the microbial cells obtained through the above-mentioned steps, the dry weight of the collected polymer, the weight ratio of the collected polymer per dried microbial cell, and the number average molecular weight, the weight average molecular weight, and the molecular weight distribution of the obtained polymer are listed together.

TABLE 13

| CDW (mg/L) | PDW (mg/L) | P/C % | Mn (×10⁴) | Mw (×10⁴) | Mw/Mn |
|---|---|---|---|---|---|
| 898 | 485 | 54.0 | 7.4 | 19.2 | 2.6 |

CDW: dry weight of microbial cells
PDW: dry weight of polymer
P/C: dry weight of polymer/dry weight of microbial cells
Mn: number average molecular weight
Mw: weight average molecular weight
Mw/Mn: molecular weight distribution The polyhydroxyalkanoate copolymer in accordance with the present invention is a novel polyhydroxyalkanoate copolymer containing: a 3-hydroxy-ω-(4-vinylphenyl)-alkanoate unit in which a 4-vinylphenyl group is substituted for the end of the side chain, as a unit having an aromatic ring and a vinyl group on its side chain; and a 3-hydroxy-ω-substituted alkanoate unit, in which a group containing a phenyl, thiophene, or cyclohexyl structure is substituted at the end of the side chain, as an additional structural unit. These two structural units are provided as main structural components, so that in general the resulting copolymer has a high glass transition temperature and maintains its satisfactory processed-product properties, which are due to the presence of the aromatic ring, and also has various reactivities, which are due to the presence of the vinyl group in the 3-hydroxy-ω-(4-vinylphenyl)-alkanoate unit. In addition, the method of manufacturing a polyhydroxyalkanoate copolymer in accordance with the present invention utilizes a microorganism to produce the copolymer as a microorganism-produced polyhydroxyalkanoate copolymer using a corresponding ω-(4-vinylphenyl)-alkanoic acid and ω-substituted alkanoic acid in which a group containing a phenyl, thiophene, or cyclohexyl structure is substituted at the end of the side chain as raw materials. The microorganism-produced polyhydroxyalkanoate copolymer contains structural unit, each having the 3' carbon atom provided as an asymmetric center. Therefore, the copolymer can be produced as an optically active substance. Specifically, in the polyhydroxyalkanoate copolymer of the present invention produced from a microorganism, the absolute configuration on the 3' carbon of each structural unit has the configuration of the R isomer. The microorganism-produced polyhydroxyalkanoate copolymer of the present invention is biodegradable due to such an absolute configuration, so that such an advantage allows the novel material to be used in a wide range of applications in addition to the biological compatibilities thereof.

What is claimed is:

1. A polyhydroxyalkanoate copolymer comprising in the same molecule:

a 3-hydroxy-ω-(4-vinylphenyl)-alkanoate unit represented by the general formula (1):

$$-\!\!\left[\mathrm{O}-\mathrm{CH}-\mathrm{CH_2}-\overset{\mathrm{O}}{\overset{\|}{\mathrm{C}}}\right]\!\!- \quad (1)$$
$$\underset{|}{(\mathrm{CH_2})_n}$$
$$\underset{|}{\mathrm{CH_2}}$$
$$\text{(4-vinylphenyl group)}$$

where n represents an integer of 0 to 7, and n independently represents the integer for each unit when the plural units are present; and at least one unit selected from the group consisting of: a 3-hydroxy-ω-substituted alkanoate unit represented by the general formula (2):

$$-\!\!\left[\mathrm{O}-\mathrm{CH}-\mathrm{CH_2}-\overset{\mathrm{O}}{\overset{\|}{\mathrm{C}}}\right]\!\!- \quad (2)$$
$$\underset{|}{(\mathrm{CH_2})_m}$$
$$\underset{|}{\mathrm{R_1}}$$

where m represents an integer of 1 to 8, and $R_1$ represents a group having a residue with a ring structure selected from a phenyl structure and a thienyl structure; and a 3-hydroxy-ω-cyclohexyl-alkanoate unit represented by the general formula (3):

$$-\!\!\left[\mathrm{O}-\mathrm{CH}-\mathrm{CH_2}-\overset{\mathrm{O}}{\overset{\|}{\mathrm{C}}}\right]\!\!- \quad (3)$$
$$\underset{|}{(\mathrm{CH_2})_k}$$
$$\text{(cyclohexyl with } R_2\text{)}$$

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which m and $R_1$ independently represent the integer and the group, respectively, for each unit when the plural units represented by the general formula (2) are present, and k and $R_2$ independently represent the integer and the substituent, respectively, for each unit when the plural units represented by the general formula (3) are present.

2. A polyhydroxyalkanoate copolymer according to claim 1, wherein:

the $R_1$ is a group selected from the group consisting of: an unsubstituted or substituted phenyl group represented by the general formula (4):

$$R_3\!\!-\!\!\text{(phenyl)}\!\!- \quad (4)$$

where $R_3$ represents a hydrogen atom, a halogen atom, a CN group, an $NO_2$ group, a $CH_3$ group, a $C_2H_5$ group, a $C_3H_7$ group, $COOR_4$ ($R_4$ represents a hydrogen atom, a sodium atom, or a potassium atom), a $CF_3$ group, a $C_2F_5$ group, or a $C_3F_7$ group;

an unsubstituted or substituted phenoxy group represented by the general formula (5):

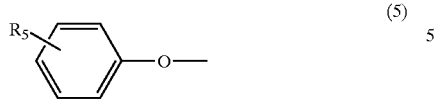
(5)

where $R_5$ represents a hydrogen atom, a halogen atom, a CN group, an $NO_2$ group, a $CH_3$ group, a $C_2H_5$ group, a $C_3H_7$ group, an $SCH_3$ group, a $CF_3$ group, a $C_2F_5$ group, or a $C_3F_7$ group;

an unsubstituted or substituted benzoyl group represented by the general formula (6):

(6)

where $R_6$ represents a hydrogen atom, a halogen atom, a CN group, an $NO_2$ group, a $CH_3$ group, a $C_2H_5$ group, a $C_3H_7$ group, a $CF_3$ group, a $C_2F_5$ group, or a $C_3F_7$ group;

an unsubstituted or substituted phenylsulfanyl group represented by the general formula (7):

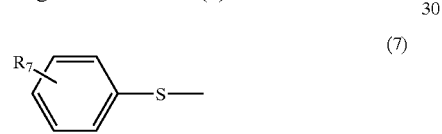
(7)

where $R_7$ represents a hydrogen atom, a halogen atom, a CN group, an $NO_2$ group, $COOR_8$, $SO_2R_9$ ($R_8$ represents H, Na, K, $CH_3$, or $C_2H_5$, and $R_9$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group;

an unsubstituted or substituted (phenylmethyl)-sulfanyl group represented by the general formula (8):

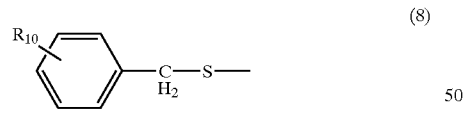
(8)

where $R_{10}$ represents a hydrogen atom, a halogen atom, a CN group, an $NO_2$ group, $COOR_{11}$, $SO_2R_{12}$ ($R_{11}$ represents H, Na, K, $CH_3$, or $C_2H_5$, and $R_{12}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group;

a 2-thienyl group represented by the general formula (9):

(9)

a 2-thienylsulfanyl group represented by the general formula (10):

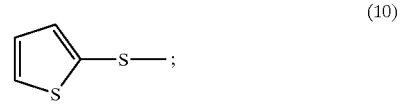
(10)

a 2-thienylcarbonyl group represented by the general formula (11):

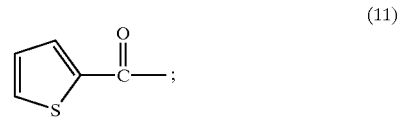
(11)

an unsubstituted or substituted phenylsulfinyl group represented by the general formula (12):

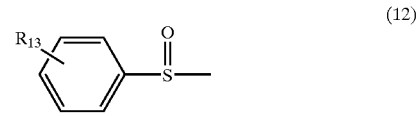
(12)

where $R_{13}$ represents a substituent for an aromatic ring and $R_{13}$ represents a hydrogen atom, a halogen atom, a CN group, an $NO_2$ group, $COOR_{14}$, $SO_2R_{15}$ ($R_{14}$ represents H, Na, K, $CH_3$, or $C_2H_5$, and $R_{15}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group;

an unsubstituted or substituted phenylsulfonyl group represented by the general formula (13):

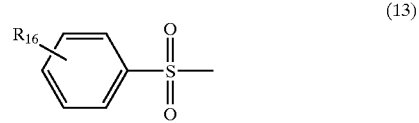
(13)

where $R_{16}$ represents a hydrogen atom, a halogen atom, a CN group, an $NO_2$ group, $COOR_{17}$, $SO_2R_{18}$ ($R_{17}$ represents H, Na, K, $CH_3$, or $C_2H_5$, and $R_{18}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group; and a (phenylmethyl)oxy group represented by the general formula (14):

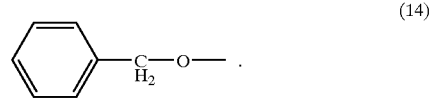
(14)

3. A polyhydroxyalkanoate copolymer according to claim 1, wherein:

the 3-hydroxy-ω-(4-vinylphenyl)-alkanoate unit represented by the general formula (1) is a 3-hydroxy-ω-(4- vinylphenyl)-valerate unit represented by the following formula (15):

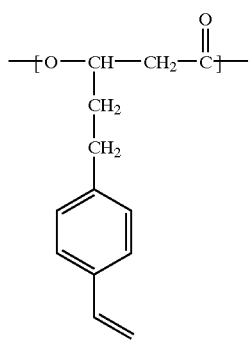

(15)

4. A polyhydroxyalkanoate copolymer according to claim 1, wherein:

the number average molecular weight of the polyhydroxyalkanoate copolymer is in a range of 2,000 to 1,000,000.

5. A method of manufacturing a polyhydroxyalkanoate copolymer that contains in the same molecule:

a 3-hydroxy-ω-(4-vinylphenyl)-alkanoate unit represented by the general formula (1):

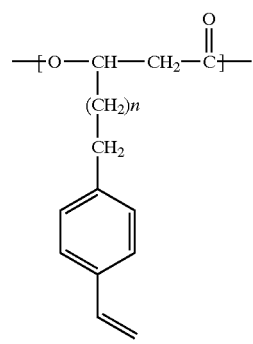

(1)

where n represents an integer of 0 to 7, and n independently represents the integer for each unit when the plural units are present; and at least one unit selected from the group consisting of: a 3-hydroxy-ω-substituted alkanoate unit represented by the general formula (19):

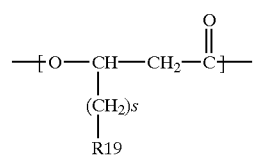

(19)

where s represents an integer of 1 to 8, and $R_{19}$ represents a group having a residue with a ring structure selected from a phenyl structure and a thienyl structure; and a 3-hydroxy-ω-cyclohexyl-alkanoate unit represented by the general formula (3):

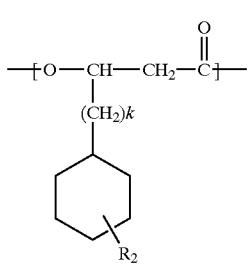

(3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which s and $R_{19}$ independently represent the integer and the group, respectively, for each unit when the plural units represented by the general formula (19) are used, and k and $R_2$ independently represent the integer and the substituent, respectively, for each unit when the plural units represented by the general formula (3) are present, the method comprising:

allowing a microorganism capable of synthesizing the polyhydroxyalkanoate copolymer from a raw material to synthesize the polyhydroxyalkanoate by making the microorganism act on the raw material including:

(A) at least one ω-(4-vinylphenyl)-alkanoic acid represented by the following general formula (16):

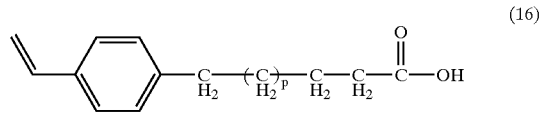

(16)

where p represents an integer of 0 to 7; and (B) at least one component selected from the group consisting of ω-substituted alkanoic acid represented by the general formula (17):

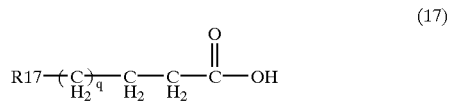

(17)

where q represents an integer of 1 to 8, and $R_{17}$ represents a group containing a residue with a ring structure selected from a phenyl structure and a thienyl structure, and ω-cyclohexyl-alkanoic acid represented by the general formula (18):

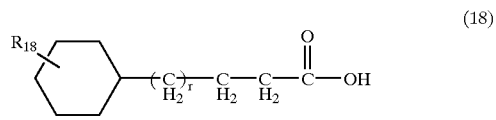

(18)

where $R_{18}$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and r represents an integer of 0 to 8.

6. A method of manufacturing a polyhydroxyalkanoate copolymer according to claim 5, wherein:

each of the $R_{17}$ and the $R_{19}$ is a group selected from the group consisting of:

an unsubstituted or substituted phenyl group represented by the general formula (20):

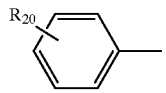

(20)

where $R_{20}$ represents a hydrogen atom, a halogen atom, a CN group, an $NO_2$ group, a $CH_3$ group, a $C_2H_5$ group, a $C_3H_7$ group, a $CF_3$ group, a $C_2F_5$ group, or a $C_3F_7$ group;

an unsubstituted or substituted phenoxy group represented by the general formula (5):

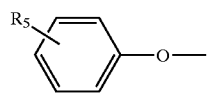

(5)

where $R_5$ represents a substituent for an aromatic ring and $R_5$ represents a hydrogen atom, a halogen atom, a CN group, an $NO_2$ group, a $CH_3$ group, a $C_2H_5$ group, a $C_3H_7$ group, an $SCH_3$ group, a $CF_3$ group, a $C_2F_5$ group, or a $C_3F_7$ group, and $R_5$ independently represents the substituent for each unit when the plural units are present;

an unsubstituted or substituted benzoyl group represented by the general formula (6):

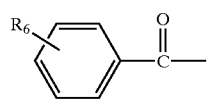

(6)

where $R_6$ represents a hydrogen atom, a halogen atom, a CN group, an $NO_2$ group, a $CH_3$ group, a $C_2H_5$ group, a $C_3H_7$ group, a $CF_3$ group, a $C_2F_5$ group, or a $C_3F_7$ group;

an unsubstituted or substituted phenyl-sulfanyl group represented by the general formula (7):

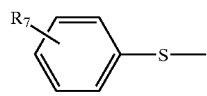

(7)

where $R_7$ represents a hydrogen atom, a halogen atom, a CN group, an $NO_2$ group, $COOR_8$, $SO_2R_9$ ($R_8$ represents H, Na, K, $CH_3$, or $C_2H_5$, and $R_9$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group;

an unsubstituted or substituted (phenylmethyl)-sulfanyl group represented by the general formula (8):

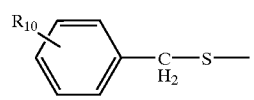

(8)

where $R_{10}$ represents a hydrogen atom, a halogen atom, a CN group, an $NO_2$ group, $COOR_{11}$, $SO_2R_{12}$ ($R_{11}$ represents H. Na, K, $CH_3$, or $C_2H_5$, and $R_{12}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group;

a 2-thienyl group represented by the general formula (9):

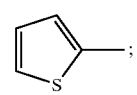

(9)

a 2-thienylsulfanyl group represented by the general formula (10):

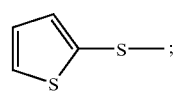

(10)

a 2-thienylcarbonyl group represented by the general formula (11):

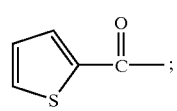

(11)

and a (phenylmethyl)oxy group represented by the general formula (14):

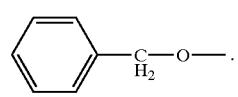

(14)

7. A method of manufacturing a polyhydroxyalkanoate copolymer according to claim 5, wherein:

the microorganism is cultured in a culture medium containing the raw material to allow the microorganism to synthesize the polyhydroxyalkanoate copolymer.

8. A method of manufacturing a polyhydroxyalkanoate copolymer according to claim 7, wherein:

the culture medium further contains at least one selected from peptides, yeast extract, organic acids and salts thereof, amino acids and salts thereof, sugars, and straight-chain alkanoic acids having 4 to 12 carbon atoms and salts thereof.

9. A method of manufacturing a polyhydroxyalkanoate copolymer according to claim 8, wherein:

polypeptone is provided as the peptides;

the organic acids and the salts thereof are each one or more compounds selected from the group consisting of pyruvic acid, oxalacetic acid, citric acid, isocitric acid, ketoglutaric acid, succinic acid, fumaric acid, malic acid, lactic acid, and salts thereof;

the amino acids and the salts thereof are each one or more compounds selected from the group consisting of glutamic acid, aspartic acid, and salts thereof; and the sugars are one or more compounds selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose.

10. A method of manufacturing a polyhydroxyalkanoate copolymer according to claim 5, further comprising:

collecting the polyhydroxyalkanoate copolymer synthesized by the microorganism from microbial cells of the microorganism.

11. A method of manufacturing a polyhydroxyalkanoate copolymer according to claim 5, wherein:

the microorganism comprises a microorganism belonging to the genus Pseudomonas.

12. A method of manufacturing a polyhydroxyalkanoate copolymer according to claim 11, wherein:

the microorganism includes at least one strain selected from the group consisting of:
Pseudomonas cichorii YN2 strain, FERM BP-7375;
Pseudomonas cichorii H45 strain, FERM BP-7374;
Pseudomonas jessenii P161 strain, FERM BP-7376; and
Pseudomonas putida P91 strain, FERM BP-7373.

13. A method of manufacturing a polyhydroxyalkanoate that contains in the same molecule: at least a 3-hydroxy-ω-(4-vinylphenyl)-alkanoate unit represented by the general formula (1):

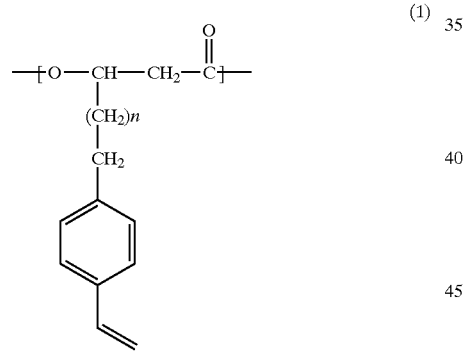

(1)

where n represents an integer of 0 to 7, and n independently represents the integer for each unit when the plural units represented by the general formula (1) are present; and at least one unit selected from the group consisting of a 3-hydroxy-ω-substituted alkanoate unit represented by the general formula (2):

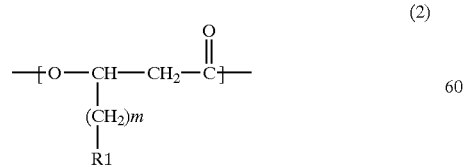

(2)

where m represents an integer of 1 to 8, and $R_1$ represents a group containing a residue with a ring structure selected from a phenyl structure and a thienyl structure, and a 3-hydroxy-ω-cyclohexyl-alkanoate acid unit represented by the general formula (3):

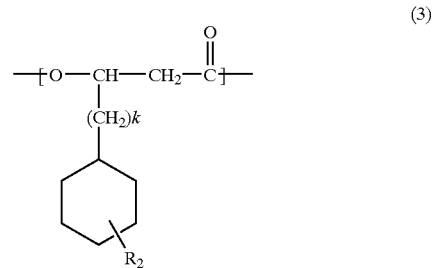

(3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which m and $R_1$ independently represent the integer and the group, respectively, for each unit when the plural units represented by the general formula (2) are present, and k and $R_2$ independently represent the integer and the substituent, respectively, for each unit when the plural units represented by the general formula (3) are present, the $R_1$ containing at least a group selected from the group consisting of a substituted phenyl group represented by the following general formula (4'), an unsubstituted or substituted phenylsulfinyl group represented by the general formula (12), and an unsubstituted or substituted phenylsulfonyl group represented by the general formula (13):

(4')

where $R_3'$ represents $COOR_4$ ($R_4$ represents a hydrogen atom, a sodium atom, or a potassium atom);

(12)

where $R_{13}$ represents a hydrogen atom, a halogen atom, a CN group, an $NO_2$ group, $COOR_{14}$, $SO_2R_{15}$ ($R_{14}$ represents H, Na, K, $CH_3$, or $C_2H_5$, and $R_{15}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group; and

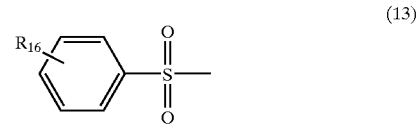

(13)

where $R_{16}$ represents a hydrogen atom, a halogen atom, a CN group, an $NO_2$ group, $COOR_{17}$, $SO_2R_{18}$ ($R_{17}$ represents H, Na, K, $CH_3$, or $C_2H_5$, and $R_{18}$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group, the method comprising one of the steps of:

(a) oxidizing a part of a vinyl group contained in a phenyl group of a group represented by the general formula (1) of a raw material to form the group represented by the general formula (4') as the $R_1$, with the raw material including a polyhydroxyalkanoate copolymer containing in the same molecule: two or more 3-hydroxy-ω-(4-vinylphenyl)-alkanoate units represented by the general formula (1):

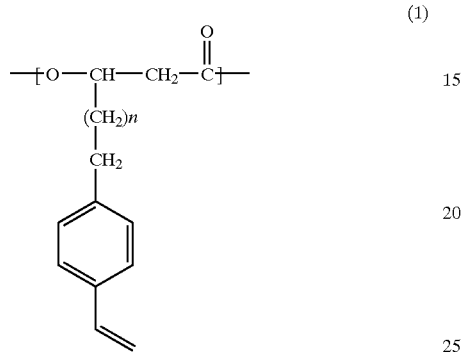

(1)

where n represents an integer of 0 to 7, and n independently represents the integer for each unit; and at least one unit selected from the group consisting of a 3-hydroxy-ω-substituted alkanoate unit represented by the general formula (19):

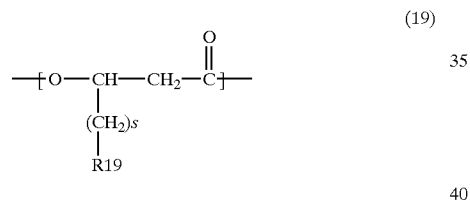

(19)

where s represents an integer of 1 to 8 and $R_{19}$ represents a group having a residue with a ring structure selected from a phenyl structure and a thienyl structure, and a 3-hydroxy-ω-cyclohexyl-alkanoate unit represented by the general formula (3):

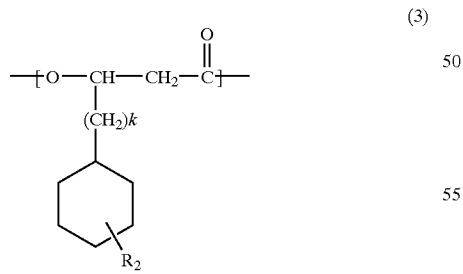

(3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which s and $R_{19}$ independently represent the integer and the group, respectively, for each unit when the plural units represented by the general formula (19) are present, and k and $R_2$ independently represent the integer and the substituent, respectively, for each unit when the plural units represented by the general formula (3) are present; and (b) selectively oxidizing —S— of the substituent represented by the general formula (7) in a polyhydroxyalkanoate copolymer provided as a raw material to be converted to a group represented by the general formula (12) or a group represented by the general formula (13), with the polyhydroxyalkanoate copolymer containing in the same molecule: a 3-hydroxy-ω-(4-vinylphenyl)-alkanoate unit represented by the general formula (1):

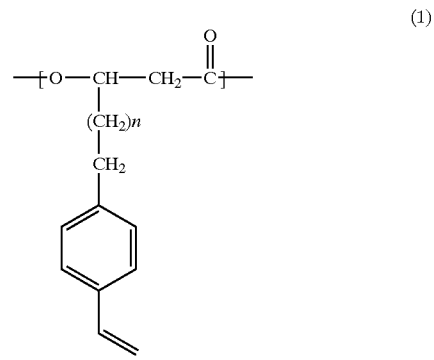

(1)

where n represents an integer of 0 to 7, and n independently represents the integer for each unit when the plural units represented by the general formula (1) are present; and at least one unit selected from the group consisting of a 3-hydroxy-ω-substituted alkanoate unit represented by the general formula (2):

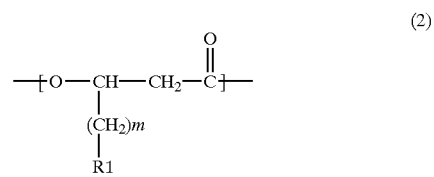

(2)

where m represents an integer of 1 to 8, and $R_1$ represents an unsubstituted or substituted phenylsulfanyl group represented by the general formula (7):

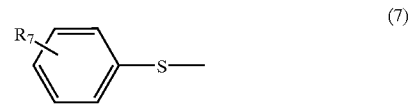

(7)

where $R_7$ represents a hydrogen atom, a halogen atom, a CN group, an $NO_2$ group, $COOR_8$, $SO_2R_9$ ($R_8$ represents H, Na, K, $CH_3$, or $C_2H_5$, and $R_9$ represents OH, ONa, OK, a halogen atom, $OCH_3$, or $OC_2H_5$), a $CH_3$ group, a $C_2H_5$ group, a $C_3H_7$ group, a $(CH_3)_2$—CH group, or a $(CH_3)_3$—C group, and a 3-hydroxy-ω-cyclohexyl-alkanoate unit represented by the general formula (3):

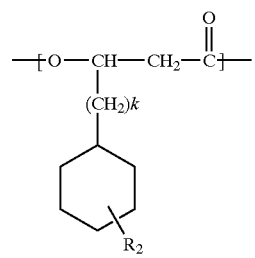 (3)

where $R_2$ represents a substituent for a cyclohexyl group and $R_2$ represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$ group, and k represents an integer of 0 to 8, in which m and $R_1$ independently represent the integer and the group, respectively, for each unit when the plural units represented by the general formula (2) are present, and k and $R_2$ independently represent the integer and the substituent, respectively, for each unit when the plural units represented by the general formula (3) are present.

14. A method of manufacturing a polyhydroxyalkanoate copolymer according to claim 13, wherein:

the oxidation in the step (a) and the oxidation in the step (b) are independently performed using at least one oxidizing agent selected from the group consisting of permanganate, dichromate, periodate, hydrogen peroxide, sodium percarbonate, metachloroperbenzoic acid, performic acid, and peracetic acid.

15. A method of manufacturing a polyhydroxyalkanoate copolymer according to claim 14, wherein:

the oxidation in each of the step (a) and the step (b) is performed using permanganate under acidic conditions.

16. A method of manufacturing a polyhydroxyalkanoate copolymer according to claim 13, wherein:

the oxidation in each of the step (a) and the step (b) is performed using ozone.

* * * * *

UNITED STATES PATENT AND TRADEMARK OFFICE
CERTIFICATE OF CORRECTION

PATENT NO. : 6,645,743 B1
DATED : November 11, 2003
INVENTOR(S) : Tsutomu Honma et al.

It is certified that error appears in the above-identified patent and that said Letters Patent is hereby corrected as shown below:

Title page, Item [54] and Column 1, line 1,
Title, "POLYHYDROXYALKANOATE" should read -- NOVEL POLYHYDROXYALKANOATE --.

Title page,
Item [56], References Cited, OTHER PUBLICATIONS, ""Bacteria Polyesters"" should read -- "Bacterial Polyesters" --.
Item [57], ABSTRACT,
Line 3, "(ω-" should read -- ω- --.

Column 6,
Lines 45-49, "  " should read -- 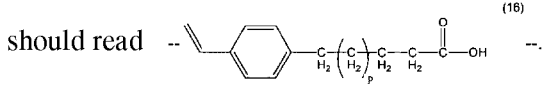 --.

Column 20,
Line 3, "La-d-Open" should read -- Laid-Open --.

Column 23,
Line 27, "four fold" should read -- a four-fold --; and
Line 29, "two fold" should read -- a two-fold --.

Column 26,
Line 21, "20c./minute." should read -- 20°C./minute. --.

Column 29,
Line 41, "x 10$^4$)" should read -- (x 10$^4$) --.

Column 33,
Line 55, "-vinylpheny)" should read -- vinylphenyl) --.

Column 36,
Line 25, "In Table 11," should read -- ¶ In Table 11, --.

Column 37,
Line 4, "having dissolved" should read -- having been dissolved --.

Column 40,
Lines 9-14, " 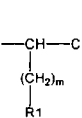 " should read -- 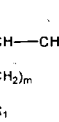 --.

UNITED STATES PATENT AND TRADEMARK OFFICE
CERTIFICATE OF CORRECTION

PATENT NO. : 6,645,743 B1
DATED : November 11, 2003
INVENTOR(S) : Tsutomu Honma et al.

It is certified that error appears in the above-identified patent and that said Letters Patent is hereby corrected as shown below:

Column 43,
Lines 57-62, [chemical structure] should read -- [corrected chemical structure] --.

Column 44,
Lines 48-51, "$R_{17}-(C_{H_2})_q-C_{H_2}-C_{H_2}-\overset{O}{\overset{\|}{C}}-OH$" should read -- $R_{17}-(C_{H_2})_q-C_{H_2}-C_{H_2}-\overset{O}{\overset{\|}{C}}-OH$ --.

Column 46,
Line 11, "represents H." should read -- represents H, --.

Column 47,
Line 30, "at least" should read -- ¶ at least --; and

Lines 58-62 [chemical structure] should read -- [corrected chemical structure] --.

Column 49,
Lines 33-38, [chemical structure] should read -- [corrected chemical structure] --.

Column 50,
Lines 42-47, [chemical structure] should read -- [corrected chemical structure] --.

Signed and Sealed this

Twenty-fourth Day of August, 2004

JON W. DUDAS
*Director of the United States Patent and Trademark Office*